US006939568B2

(12) United States Patent
Burrell et al.

(10) Patent No.: US 6,939,568 B2
(45) Date of Patent: Sep. 6, 2005

(54) TREATMENT OF INFLAMMATORY SKIN CONDITIONS

(75) Inventors: Robert Edward Burrell, Sherwood Park (CA); Hua Qing Yin, Sherwood Park (CA)

(73) Assignee: Nucryst Pharmaceuticals Corp., Fort Saskatchewan (CA)

( * ) Notice: Subject to any disclaimer, the term of this patent is extended or adjusted under 35 U.S.C. 154(b) by 106 days.

(21) Appl. No.: 10/131,511

(22) Filed: Apr. 23, 2002

(65) Prior Publication Data

US 2003/0054046 A1 Mar. 20, 2003

Related U.S. Application Data

(63) Continuation-in-part of application No. 09/840,637, filed on Apr. 23, 2001.
(60) Provisional application No. 60/285,884, filed on Apr. 23, 2001.

(51) Int. Cl.$^7$ .......................... A61K 33/00; A61K 33/24; A61K 33/38; A61K 31/28; A61K 31/282; A61K 31/295; A61K 9/00; A61K 9/14; A61P 17/00; A61P 17/02

(52) U.S. Cl. .......................... 424/618; 424/59; 424/400; 424/402; 424/404; 424/405; 424/484; 424/485; 424/488; 424/489; 424/490; 424/600; 424/604; 424/617; 424/619; 424/630; 424/631; 424/632; 424/633; 424/634; 424/635; 424/637; 424/638; 424/641; 424/642; 424/643; 424/646; 424/649; 424/650; 424/651; 424/653; 514/492; 514/493; 514/494; 514/495; 514/499; 514/500; 514/503; 514/829; 514/830; 514/861; 514/862; 514/864; 514/865; 514/880; 514/881; 514/886; 514/887; 514/944; 514/951; 514/964

(58) Field of Search .......................... 424/59, 400, 402, 424/404, 405, 484, 485, 488–490, 600, 604, 617–619, 630–635, 637–638, 641–643, 646, 649–651, 653; 514/492–495, 499–500, 503, 829–831, 858–865, 880, 881, 886, 887, 944, 951, 964, 859, 825, 870, 871, 918, 919

(56) References Cited

U.S. PATENT DOCUMENTS

| | | |
|---|---|---|
| 3,757,786 A | 9/1973 | Smith |
| 3,800,792 A | 4/1974 | McKnight et al. .......... 128/156 |
| 3,918,446 A | 11/1975 | Buttaravoli |
| 4,059,105 A | 11/1977 | Citruzzula et al. |
| 4,324,237 A | 4/1982 | Buttaravoli |
| 4,355,636 A | 10/1982 | Oetjen et al. |
| 4,476,590 A | 10/1984 | Scales et al. |
| 4,581,028 A | 4/1986 | Fox, Jr. et al. |
| 4,596,556 A | 6/1986 | Morrow et al. |
| 4,633,863 A | 1/1987 | Filips et al. |
| 4,749,572 A | 6/1988 | Ahari .......... 424/132 |
| 4,790,824 A | 12/1988 | Morrow et al. |
| 4,803,066 A | 2/1989 | Edwards .......... 424/132 |
| 4,828,832 A | 5/1989 | De Cuellar et al. |
| 4,847,049 A | 7/1989 | Yamamoto |
| 4,952,411 A | 8/1990 | Fox, Jr. et al. .......... 424/618 |
| 4,960,413 A | 10/1990 | Sagar et al. |
| 5,019,096 A | 5/1991 | Fox, Jr. et al. |
| 5,064,413 A | 11/1991 | McKinnon et al. |
| 5,122,418 A | 6/1992 | Nakane et al. |
| 5,143,717 A | 9/1992 | Davis |

(Continued)

FOREIGN PATENT DOCUMENTS

| | | | |
|---|---|---|---|
| CA | 2242033 | 1/1999 | |
| CN | 1082645 | 2/1994 | .......... D06M/11/83 |
| CN | 1241662 | 1/2000 | .......... D06M/11/83 |
| CN | 1262093 | 8/2000 | .......... A61K/7/02 |
| CN | 1279222 | 1/2001 | .......... C04B/41/85 |
| CN | 1291666 | 4/2001 | .......... D06M/11/58 |
| CN | 1291667 | 4/2001 | .......... D06M/13/144 |
| CN | 1306117 | 8/2001 | .......... D06M/11/58 |
| CN | 1322474 | 11/2001 | .......... A01N/59/16 |
| CN | 1322874 | 11/2001 | .......... D06M/11/83 |
| CN | 1328819 | 1/2002 | .......... A61K/9/70 |
| CN | 1328827 | 1/2002 | .......... A61K/33/38 |
| DE | 2748882 | 5/1979 | |
| DE | 3807944 | 9/1989 | |

(Continued)

OTHER PUBLICATIONS

Hoet, Peter H.M. et al., "Nanoparticles—known and unknown health risks," Journal of Nanobiotechnology, vol. 2, Dec. 8, 2004, pp. 1–15.*
Borm, Paul J.A. et al., "Toxicological hazards of inhaled nanoparticles—potential implications for drug delivery," Journal of Nanoscience and Nanotechnology, vol. 4(5), 2004, pp. 521–531.*
Ozkan, M., "Quantum dots and other nanoparticles: what can they offer to drug discovery?" Drug Discovery Today, vol. 9(24), Dec. 2004, pp. 1065–1071.*
Williams, D., "Nanocrystalline metals: another opportunity for medical devices?" Medical Device Technology, vol. 14(9), Nov. 2003, p. 12 (pp. 1–4 in the copy obtained via ProQuest).*
Sant et al., "Morphology of Novel Antimicrobial Silver Films Deposited By Magnetron Sputtering" Scripta Materiala, vol. 41, No. 12, pp. 1333–1339, Nov. 19, 1999.

(Continued)

Primary Examiner—John Pak
(74) Attorney, Agent, or Firm—Fish & Richardson P.C.

(57) ABSTRACT

The invention relates to the use of one or more antimicrobial metals, most preferably silver, preferably formed with atomic disorder, and preferably in a nanocrystalline form, for the treatment of inflammatory skin conditions. The nanocrystalline antimicrobial metal of choice may be used in the form of a nanocrystalline coating of one or more antimicrobial metals, a nanocrystalline powder of one or more antimicrobial metals, or a solution containing dissolved species from a nanocrystalline powder or coating of one or more antimicrobial metals.

53 Claims, 2 Drawing Sheets

U.S. PATENT DOCUMENTS

| | | | |
|---|---|---|---|
| 5,236,421 A | 8/1993 | Becher | |
| 5,270,358 A | 12/1993 | Asmus | 524/55 |
| 5,312,335 A | 5/1994 | McKinnon et al. | |
| D349,958 S | 8/1994 | Hollis et al. | |
| 5,369,155 A | 11/1994 | Asmus | 524/55 |
| 5,372,589 A | 12/1994 | Davis | |
| 5,383,851 A | 1/1995 | McKinnon, Jr. et al. | |
| 5,399,163 A | 3/1995 | Peterson et al. | |
| 5,454,886 A | 10/1995 | Burrell et al. | |
| 5,454,889 A | 10/1995 | McNicol et al. | |
| 5,457,015 A | 10/1995 | Boston | |
| 5,520,639 A | 5/1996 | Peterson et al. | |
| 5,534,288 A | 7/1996 | Gruskin et al. | |
| 5,563,132 A | 10/1996 | Bodaness | |
| 5,569,207 A | 10/1996 | Gisselberg et al. | |
| 5,578,073 A | 11/1996 | Haimovich et al. | |
| 5,631,066 A | 5/1997 | O'Brien | |
| 5,681,575 A | 10/1997 | Burrell et al. | |
| 5,744,151 A | 4/1998 | Capelli | 424/405 |
| 5,753,251 A | 5/1998 | Burrell et al. | |
| 5,770,255 A | 6/1998 | Burrell et al. | 427/2.1 |
| 5,770,258 A | 6/1998 | Takizawa | |
| 5,792,793 A | 8/1998 | Oda et al. | 514/495 |
| 5,837,275 A | 11/1998 | Burrell et al. | |
| 5,848,995 A | 12/1998 | Walder | |
| 5,895,419 A | 4/1999 | Tweden et al. | |
| 5,899,880 A | 5/1999 | Bellhouse et al. | |
| 5,945,032 A | 8/1999 | Breitenbach et al. | 252/186.29 |
| 5,958,440 A | 9/1999 | Burrell et al. | |
| 5,981,822 A | 11/1999 | Addison | |
| 5,985,308 A | 11/1999 | Burrell et al. | |
| 6,010,478 A | 1/2000 | Bellhouse et al. | |
| 6,013,050 A | 1/2000 | Bellhouse et al. | |
| 6,017,553 A | 1/2000 | Burrell et al. | |
| 6,022,547 A | 2/2000 | Herb et al. | 424/401 |
| 6,071,541 A | 6/2000 | Murad | 424/616 |
| 6,071,543 A | 6/2000 | Thornfeldt | 424/642 |
| 6,096,002 A | 8/2000 | Landau | |
| 6,123,925 A | 9/2000 | Barry et al. | |
| 6,126,931 A | 10/2000 | Sawan et al. | 424/78.09 |
| 6,165,440 A | 12/2000 | Esenaliev | |
| 6,187,290 B1 | 2/2001 | Gilchrist et al. | 424/45 |
| 6,197,351 B1 | 3/2001 | Neuwirth | |
| 6,201,164 B1 | 3/2001 | Wulff et al. | 602/48 |
| 6,224,898 B1 | 5/2001 | Balogh et al. | 424/445 |
| 6,238,686 B1 | 5/2001 | Burrell et al. | |
| 6,258,385 B1 | 7/2001 | Antelman | 424/618 |
| 6,277,169 B1 | 8/2001 | Hampden-Smith et al. | |
| 6,294,186 B1 | 9/2001 | Beerse et al. | |
| 6,333,093 B1 | 12/2001 | Burrell et al. | |
| 6,365,130 B1 | 4/2002 | Barry et al. | |
| 6,692,773 B2 * | 2/2004 | Burrell et al. | 424/618 |
| 6,720,006 B2 | 4/2004 | Hanke et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | 424/618 |
| 2002/0045049 A1 | 4/2002 | Madsen | |
| 2002/0051824 A1 | 5/2002 | Burrell et al. | |
| 2002/0192298 A1 | 12/2002 | Burrell et al. | |

FOREIGN PATENT DOCUMENTS

| | | | |
|---|---|---|---|
| DE | 195 41 735 A1 | 5/1997 | |
| EP | 136 768 | 4/1985 | A61K/33/38 |
| EP | 254 413 | 1/1988 | A61K/33/38 |
| EP | 0 356 060 | 8/1989 | |
| EP | 355 009 | 2/1990 | A61K/31/635 |
| EP | 378 147 | 7/1990 | A61K/7/48 |
| EP | 599 188 | 6/1994 | A61K/31/20 |
| EP | 0 681 841 A1 | 11/1995 | |
| EP | 0681841 | 11/1995 | |
| EP | 0780138 | 6/1997 | |
| EP | 0 328 421 A2 | 8/1999 | |
| EP | 1 159 972 | 12/2001 | A61L/15/18 |
| GB | 420052 | 11/1934 | |
| GB | 427106 | 4/1935 | |
| GB | 965010 | 7/1964 | |
| GB | 1270410 | 4/1972 | |
| GB | 2 073 024 | 10/1981 | |
| GB | 2 140 684 | 12/1984 | A61K/35/06 |
| HU | 980078 A | 9/1999 | |
| IT | 22309A/90 | 12/1990 | |
| JP | 60-21912 | 2/1985 | |
| JP | SHO 58-126910 | 2/1985 | |
| JP | 04244029 A | 9/1992 | |
| JP | 11 060493 A | 3/1999 | |
| JP | 11060493 | 3/1999 | |
| JP | 11116488 | 4/1999 | |
| JP | 11 116488 | 4/1999 | |
| JP | 11124335 | 5/1999 | |
| JP | 11 124335 | 5/1999 | |
| JP | 2000 327578 | 11/2000 | |
| JP | 2000327578 | 11/2000 | |
| WO | 87/07251 | 12/1987 | |
| WO | WO 89/09054 | 10/1989 | |
| WO | 92/13491 | 8/1992 | |
| WO | WO 93/23092 | 11/1993 | A61L/29/00 |
| WO | 93/23092 | 11/1993 | |
| WO | 95/13704 | 5/1995 | |
| WO | WO 95/13704 | 5/1995 | A01N/59/16 |
| WO | 98/41095 | 9/1998 | |
| WO | WO 98/41095 | 9/1998 | A01N/59/00 |
| WO | 98/51273 | 11/1998 | |
| WO | 00/27390 | 5/2000 | |
| WO | WO 00/27390 | 5/2000 | |
| WO | 00/30697 | 6/2000 | |
| WO | 00/44414 | 8/2000 | |
| WO | 00/64505 | 11/2000 | |
| WO | 00/64506 | 11/2000 | |
| WO | WO 00/78281 | 12/2000 | A61K/7/48 |
| WO | WO 00/78282 | 12/2000 | A61K/7/48 |
| WO | 01/15710 | 3/2001 | |
| WO | 01/24839 | 4/2001 | |
| WO | WO 01/26627 | 4/2001 | A61K/9/127 |
| WO | 01/27365 | 4/2001 | |
| WO | 01/34686 | 5/2001 | |
| WO | 01/41774 | 6/2001 | |
| WO | 01/41819 | 6/2001 | |
| WO | WO 01/41819 | 6/2001 | A61L/15/28 |
| WO | 01/43788 | 6/2001 | |
| WO | WO 01/49115 | 7/2001 | A01N/25/34 |
| WO | WO 01/49301 | 7/2001 | |
| WO | 01/49301 | 7/2001 | |
| WO | WO 01/49302 | 7/2001 | A61K/33/00 |
| WO | WO 01/49303 | 7/2001 | A61K/33/00 |
| WO | 01/68179 A1 | 9/2001 | |
| WO | 01/70052 | 9/2001 | |
| WO | WO 01/74300 | 10/2001 | A61K/6/00 |
| WO | 01/80920 | 11/2001 | |
| WO | WO 02/09729 A2 | 2/2002 | |
| WO | 02/09729 | 2/2002 | |
| WO | 02/15698 | 2/2002 | |
| WO | 02/18003 | 3/2002 | |
| WO | WO 02/18699 | 3/2002 | D06M/11/83 |
| WO | 02/44625 | 6/2002 | |

OTHER PUBLICATIONS

Burrell, et al. "Efficacy of Silver–Coated Dressings as Bacterial Barriers in a Rodent Burn Sepsis Model" *Wounds* 1999, 11(4):64–71.

Demling, et al., "The Role of Silver in Wound Healing: Effects of Silver on Wound Management," *Wounds*, vol. 13, No. 1, Jan./Feb. 2001 Supplement A; pp. 5–14.

Djokic et al., "An Electrochemical Analysis of Thin Silver Films Produced by Reactive Sputtering", *Journal of The Electrochemical Society*, 148(3) C191–C196 (2001).

International Search Report PCT/CA 02/00549 dated Nov. 11, 2002.

Kirsner, et al., "The Role of Silver in Wound Healing: Matrix Metalloproteinases in Normal and Impaired Wound Healing: A Potential Role of Nanocrystalline Silver," *Wounds*, vol. 13, No. 3, May/Jun. 2001, Supplement C pp. 5–12.

Olson et al., "Healing of Porcine Donor sites Covered with Silver–coated Dressings" * *Eur J Surg* 2000; 166: 486–489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5–10.

Sant et al., "Novel duplex antimicrobial silver films deposited by magnetron sputtering", *Philosophical Magazine Letters*, 2000, vol. 80, No. 4, 249–256.

Tredget , "Evaluation of Wound Healing using Silver Dressing", Feb. 26, 1996.

Tredget et al., "A Matched–Pair, Randomized Study Evaluating the Efficacy and Safety of Acticoat* Silver–Coated Dressing for the Treatment of Burn Wounds," *Journal of Burn Care & Rehabilitation* Nov./Dec. 1998; 19:531–7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11–20.

Wright et al., "Early healing events in a porcine model of contaminated wounds: effects of nanocrystalline silver on matrix metalloproteinases, cell apoptosis, and healing" *Wound Repair and Regeneration* 2002; 10:141–151.

Wright, et al., "The Comparative Efficacy of Two Antimicrobial Barrier Dressings: In–vitro Examination of Two Controlled Release of Silver Dressings" *Wounds* vol. 10, No. 6 Nov./Dec. 1998, pp. 179–188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572–577 Dec. 1998.

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2 Jan./Feb. 1999.

Merle E. Olson et al "Healing of Porcine Donor Sites Covered with Silver–Coated Dressings", Eur J Surg 2000; 166:486–489.

John A. Thornton "Influence of Apparatus Geometry and Deposition Conditions on the Structure and Topography of Thick Sputtered Coatings", J. Vac. Sci, Technol. vol. 11, No. 4 Jul./Aug. 1974 p. 666–670.

Shigemasa et al., "Applications of Chitin and Chitosan for Biomaterials" *Biotechnology & Genetic Engineering Reviews* vol. 13 (14) pp. 383–420.

Thornton, "Deposition Technologies for Films and Coatings: Coating Deposition by Sputtering" *Materials Science Series* 5 pp. 170–243 1982.

WPIDS abstract 1966–11488F (1966).

WPIDS abstract 1989–312257 (1989).

Medline abstract, accession No. 96064219 (1996).

WPIDS abstract 1966–11488F (1966).

WPIDS abstract 1989–312257 (1989).

Medline abstract, accession No. 96064219 (1996).

* cited by examiner

TREATMENT OF INFLAMMATORY SKIN CONDITIONS

CROSS-REFERENCE TO RELATED APPLICATIONS

This application is a Continuation-in-Part of co-pending U.S. patent application Ser. No. 09/840,637 filed Apr. 23, 2001. This application also claims priority from U.S. Provisional Patent Application No. 60/285,884, filed Apr. 23, 2001. To the extent that they are consistent herewith, the aforementioned applications are incorporated herein by reference.

FIELD OF THE INVENTION

The invention relates to the use of antimicrobial metals for the treatment of inflammatory skin conditions.

BACKGROUND OF THE INVENTION

Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function. As used herein, inflammatory skin conditions include, but are not limited to, eczema and related conditions, insect bites, erythroderma, mycosis fungoides and related conditions, pyoderma gangrenosum, erythema multiforme, rosacea, onychomycosis, and acne and related conditions, but excluding psoriasis and its related conditions. The following is an overview of these inflammatory skin conditions.

I Eczema and Related Conditions

Eczema relates to a group of conditions characterized by varying degrees of itching, redness, scaling, and blistering of the skin. Eczema occurs as a reaction to many endogenous and exogenous agents, and is characterized in the acute stage by erythema, edema associated with a serious exudate between the cells of the epidermis and an inflammatory infiltrate in the dermis, oozing and vesiculation, crusting and scaling. Chronic stages are characterized by thickened skin areas with accentuated skin markings, signs of traumatized or abraded skin caused by scratching, and hyperpigmentation or hypopigmentation or both. The various types of eczema include the following:

i) Atopic eczema is the most common type of eczema. Atopic eczema is a chronic, pruritic, superficial inflammation of the skin, frequently associated with a personal or family history of allergic disorders such as hay fever and asthma. Topical or oral corticosteroids, or antihistamines are common treatments.

ii) Acrodermatitis continua is characterized by painful, often disabling, lesions on the fingertips or the tips of the toes. The nails may become deformed, and the disease can damage bone in the affected area. Treatment may include topical corticosteroids and systemic remedies, such as retinoids or psoralen-UVA, although is difficult due to the rarity of the disease.

iii) Contact allergic dermatitis is acute or chronic dermatitis caused by materials or substances coming into contact with the skin, which may involve either allergic or non-allergic mechanisms. Materials or substances known to induce contact allergic dermatitis include plant substances such as poison ivy, metals such as nickel or chromium, cosmetics, rubber compounds or chemicals.

iv) Contact irritant dermatitis is a nonallergic type of contact dermatitis caused by intense or long term exposure to a substance which directly damages the skin. Following exposure, skin inflammation can occur immediately or gradually after repeated exposure; for example, sunburn caused by overexposure to ultraviolet light; or exposure to acids and alkalis in household cleaning products.

v) Dyshydrotic eczema or pompholyx is a chronic condition characterized by deep-seated pruritic vesicles on the palms, sides of the fingers, and soles. Scaling, redness, and oozing often follow vesiculation. Secondary infection with Staphylococcal bacteria is frequent. Treatments include topical steroids and cold compresses, or oral steroids for acute cases.

vi) Lichen simplex chronicus is a chronic, superficial, pruritic inflammation of the skin, characterized by dry, scaling, well-demarcated, hyperpigmented, thickened skin with accentuated markings of oval, irregular, or angular shape. The pruritus may be controlled most effectively with topical corticosteroids.

vii) Nummular eczema is characterized by discrete, coin-shaped, ringed or annular lesions which may coalesce to form extensive patches, which may ooze and crust over, and affects the extensor surfaces of the extremities, lower legs, chest, back and buttocks. No treatment is uniformly effective. Oral antibiotics or corticosteroid creams are generally used as treatments. In more resistant cases, ultraviolet B radiation alone or ultraviolet A with oral psoralen may be helpful.

viii) Seborrheic dermatitis is chronic and characterized by moderate erythema; dry, moist or greasy scaling; itching; and yellow crusted patches on areas of the body with high densities of large oil glands, especially the face and scalp. Treatment with zinc pyrithione, selenium sulfide, sulfur and salicylic acid, tar shampoo, or a corticosteroid lotion is common.

ix) Stasis eczema is a chronic inflammation of the skin of the lower legs, commonly associated with venous incompetency. Edema, erythema, mild scaling, and brown discoloration occur. Elevating the ankle above the heart while resting, wearing properly fitted support hose, and applying topical therapy are necessary. However, unless circulation improves, these approaches will be relatively ineffective. The choice of topical therapy depends upon the disease stage, with therapies including compresses, dressings, and corticosteroid creams.

II Insect Bites

Insect bites or stings can produce localized pain, redness, swelling and itching of the skin. In serious cases, complications include allergic reaction, infection, disease, reaction to venom, toxic reaction, or shock. Depending upon the specific insect, treatments may include rest and elevation, local application of ice packs and lotions, analgesics, antihistamines, or hospitalization for life threatening, anaphylactic reactions.

III Erythroderma

Erythroderma relates to any dermatitis where erythema (abnormal redness of the skin) occurs. Erythroderma, involving more than 90% of the skin, is potentially life threatening for a patient, since the barrier function of the skin has been lost. Hospitalization, topical moisturisers and intravenous fluids may be required to maintain hydration of the patient.

IV Mycosis Fungoides and Related Conditions

Mycosis fungoides is an uncommon chronic T-cell lymphoma primarily affecting the skin and occasionally the internal organs. Mycosis fungoides is rare, appearing as a chronic, pruritic rash which is difficult to diagnose. Initially plaquelike, it may spread to involve most of the skin, become nodular, and eventually become systemic. Lesions may become ulcerated. Pathologic diagnosis is delayed because sufficient quantities of lymphoma cells appear in the skin lesions very gradually. Treatment is temporarily effective, and may include psoralen-UVA, cortisone ointments for mild cases, nitrogen mustard, and photochemotherapy.

V Pyoderma Gangrenosum

Pyoderma gangrenosum is characterized by relatively indolent ulcers with extensive necrosis around the edges of the lesions on the lower extremities of the body. While pyoderma gangrenosum may be an isolated finding, it is most often associated with ulcerative colitis or Crohn's disease. The ulcers have ragged bluish-red overhanging edges and a necrotic base. The lesions often start as pustules or tender nodules at the site of trauma, and then gradually increase in size until liquefaction necrosis occurs and an irregular ulcer develops. The ulcers are often multiple and may cover large areas of the leg. Treatments include topical steroids, anti-inflammatory antibiotics, and oral steroids for more severe cases.

VI Erythema Multiforme

Erythema multiforme is an inflammatory eruption characterized by symmetric erythematous, edematous, or bullous lesions of the skin or mucous membranes. Erythema multiforme may be induced by an infectious disease (e.g., herpes simplex, *Mycoplasma pneumoniae*); drug therapy (e.g., penicillin, sulfonamides, and barbiturates); or a vaccine (e.g., Bacille Calmette-Guérin, poliomyelitis vaccines). The mechanism by which diseases, drugs, or vaccines cause erythema multiforme is unknown, but it is generally considered a hypersensitivity reaction. Treatments include mild topical cortisone, colloidal baths, and wet compresses.

VII Rosacea

Rosacea is a chronic inflammatory disorder, usually beginning in middle age or later and characterized by prominent cutaneous blood vessels, erythema, papules, and pustules primarily in the central areas of the face. Tissue hypertrophy, particularly of the nose, may result. Rarely, rosacea occurs on the trunk and extremities. The cause is unknown, but the disease is most common in persons with a fair complexion. Rosacea may resemble acne, but comedones are never present. Treatments include topical metronidazole for three months or oral antibiotics. Laser treatments may be required to remove tissue hypertrophy.

VIII Onychomycosis

Onychomycosis is an infection that causes fingernails or toenails to thicken, discolor, disfigure, and split. Thick toenails cause discomfort in shoes and make standing and walking painful for the patient. If the problem is caused by bacteria such as staphylococcus, streptococcus, and pseudomonas, the condition is called paronychia. In most cases, paronychia infections can be differentiated from onychomycosis by the inflammation they cause to the skin adjacent to the nail. Onychomycosis is caused most commonly by fungi known as dermatophytes (*Trichophyton rubrum* and *Trichophyton mentagrophytes*), and less commonly by yeasts (*Candida albicans* causes fingernail infections), and molds (Scopulariopsis, Fusarium). Infections caused by dermatophytes are generally limited to the nail, but may spread to the surrounding skin and cause inflammation. The four types of onychomycosis include distal and/or lateral subungual onychomycosis affecting the nail bed and nail plate; proximal subungual onychomycosis affecting the proximal nail fold with infection extending distally under the nail plate; superficial white onychomycosis affecting the top of the nail plate; and candidal onychomycosis affecting the nail and skin. Onychomycosis is difficult to treat, in that secondary skin infections including paronychia, and recurrent fungal infections of the nails or other parts of the body may occur. Oral medications such as Lamisil™ (terbinafine) or Sporanox™ (itraconazole) may produce adverse side effects in the liver, while topical treatments tend to be ineffective. Further, oral and topical medications work gradually, requiring several months to completely eliminate the infection.

IX Acne and Related Conditions

The term "acne" is a general term to denote inflammatory disorders of the pilosebaceous unit. Acne is a group of disorders whose initial pathology is the comedo and includes acne vulgaris (common acne), neonatal acne, infantile acne, and pomade acne. Acne commonly afflicts adolescents and young adults; however, there is growing number of patients who develop acne in their late twenties or thirties. There are data that suggest a familial or genetic tendency for patients to develop severe cystic or conglobate acne. Additionally, acne has been linked to endocrine disorders, especially those characterized by elevated levels of circulating testosterone or testosterone congeners. Exogenous agents that could exacerbate acne include medications e.g. iodides, antiseizure, certain antibiotics and corticosteroids.

Acne is a chronic inflammatory disorder affecting the sebaceous glands. Acne lesions primarily involve the sebaceous glands located on the face, neck, chest and back. Both closed comedones (blackheads) and open comedones (whiteheads) are caused by hyperkeratinization of the infundibulum of the sebaceous duct. These keratinous plugs block the flow of sebum. These dilated ducts abound with the colonies of *Propionibacterium acnes* and other fat splitting organisms. The clinically evident open and closed comedones and the microscopic microcomedo are the signal lesions of acne. The acne process results from a cascade of events. First, at puberty a spike in androgen production heralds an increase in sebum production and begins the hyperkeratinization process causing microcomedones and sebum blockade. With this blockage, the number of resident follicular flora increases dramatically. These bacteria produce inflammatory products, which permeate through thin walls of dilated sebum-filled duct. Once in the perifollicular dermis, they trigger the body's own immune defenses (both acute and granulaomatous) to produce the characteristic inflammatory papules, pustules and nodules characteristic of inflammatory acne.

Increased sebum production; comedo formation, in which the follicular infundibulum hypercomifies, hyperkeratinizes, and hypodesquamates; colonization of the follicule by anaerobic *Propionibacterium* (mainly *P. acnes*); and the host's inflammatory response are generally believed to contribute to the development of acne. These four factors are interrelated. Sebum is comedogenic and causes inflammation by itself. The *Propionibacterium* has high lipolytic activity and liberates free fatty acids from sebum lipids, whereby the free fatty acids have been shown to cause marked inflammation. The microorganisms also produce other extracellular enzymes such as proteases and hyaluronidases, and chemotactic factors, which may be important in the inflammatory process. Aside from these factors, serum hormones, especially dehydroepiandrosterone sulfate, have been found to correlate with acne.

Acne treatments generally target the keratinous plugs in sebaceous ducts; large sebaceous glands producing excess sebum; increased numbers of resident follicular bacteria; and inflammatory response to chemical mediators passing through the follicular wall. Most acne treatments are directed at preventing inflammatory lesions, particularly the larger nodulo-cystic lesions which tend to be destructive and lead to permanent scarring. In general, visible comedones are the only minor cosmetic nuisances and do not lead to inflammatory lesions.

Topical products used to remove comedones ("comedolytics") include tretinoin (Retin A™), adapalene 0.1% (Differin™), sodium sulfacetamide 10%/sulfur 5% (Sulfacet-R™), and salicylic acid 2%. A naturally occurring metabolite of Vitamin A, tretinoin or all-trans retinoic acid increases epidermal cell turnover and prevents the formation of new keratinous plugs. Application of tretinoin is normally once nightly. Although tretinoin is the most effective comedolytic, dryness, stinging and redness may occur, and improvement takes 6–8 weeks. Adapalene 0.1% is a topical retinoid-like tretinoin and is usually applied once nightly. Side effects include frequent scaling, burning, redness and dryness, and improvement takes 4–8 weeks. Sodium sulfacetamide 10%/sulfur 5% is both an antibacterial and comedolytic lotion, with improvement taking 4–8 weeks. Salicylic acid 2% exhibits mild activity.

For severe cystic or conglobate acne, isotretinoin (Accutane™), which is a metabolite of Vitamin A, is administered orally. Isotretinoin has effective anti-sebum activity, but is teratogenic (causing birth defects), and hepatotoxic (elevating triglycerides and total cholesterol and decreasing high-density lipoproteins). Other side effects include dry skin, dry eyes, itching, headaches, nosebleed, and photosensitivity. Improvement takes 4–5 months. Since estrogens also have anti-sebum activity, acne may also be treated with oral contraceptive pills.

Topical and/or oral antimicrobial agents may also be used to decrease bacteria that colonize the follicular duct. Topical agents include benzoyl peroxide (BP), and BP 5%/erythromycin 3% (Benzamycin™). BP is often tried first for both non-inflammatory and mild inflammatory acne, but can produce erythema and peeling, and improvement takes 1–2 months. Topical antibiotics include clindamycin and erythromycin, with improvements taking 1–2 months. Azelaic acid 20% (Azelex™) has mild antibacterial effects. Further, systemic antibiotics include tetracycline and its analogs (doxycycline and minocycline), which are used in low doses for years or until the end of the acne prone years. However, bacterial resistance may occur, such that the antibiotics need to be changed or substituted with BP.

Intralesional corticosteroids and topical nicotinamide have also been used to control a host's inflammatory response. There are no drugs that directly affect the inflammatory acne. The retinoids do have some anti-inflammatory properties, but these are poorly described. Topical steroid and even systemic steroids have been used to abort a severe flare of fulminant acne, but have undesirable side effects.

Treatments for Inflammatory Skin Conditions

While a range of treatments have been developed for inflammatory skin conditions, none are completely effective or free of adverse side effects. As outlined above, treatments for different inflammatory skin conditions typically include topical or oral steroids (e.g., for various types of eczema, acne, and erythema multiforme); ultraviolet light (e.g., for nummular eczema and mycosis fungoides); or other anti-inflammatory therapies. However, such treatments may be ineffective, provide only temporary relief, have deleterious side effects, or take months to treat. As an example, no treatment is uniformly effective for nummular eczema or stasis eczema. Current treatments for mycosis fungoides are only temporarily effective. Oral steroids have significant side effects, such that the severity of the skin disease must be carefully assessed. While short term treatment (a few days or weeks) with oral steroids is relatively safe, long term treatment (more than 3 months) may cause undesirable side effects including Cushing's syndrome, skin thinning, and increased susceptibility to infection. Improvements may be delayed, such as with the various acne treatments lasting several months.

While the patent literature reports that silver metal or silver salts such as silver nitrate, silver halides or silver sulphadiazine are among useful antibacterial agents for skin treatment, they have not, to the inventor's knowledge, been widely adopted for treatment of inflammatory skin conditions. In some inflammatory conditions, secondary infection is a possibility; thus, a treatment which contributes both anti-inflammatory and antimicrobial effects is advantageous. Further, there still exists a need for the treatment of inflammatory skin conditions including eczema, acne, and other related inflammatory skin conditions, with such a treatment being effective, lacking undesirable side effects, and showing improvement without a lengthy delay.

SUMMARY OF THE INVENTION

Through research, the inventors have established that crystalline antimicrobial metals such as nanocrystalline silver, preferably formed with atomic disorder, are effective antimicrobial agents against bacteria associated with inflammatory skin conditions such as acne. Further, the inventors have established through clinical observations with acne and eczema patients, and in animal experiments for allergic contact dermatitis, that antimicrobial metals such as silver, formed with atomic disorder, also reduce the inflammatory reaction. Further, the inventors have demonstrated that antimicrobial metals such as silver, formed with atomic disorder, can alleviate erythema and edema, which are characteristic symptoms of many inflammatory skin conditions. This research has resulted in a new therapeutic treatment for acne, eczema, and other inflammatory skin conditions. In some inflammatory conditions, secondary infection by bacteria or other microbiological agents is a possibility. When the antimicrobial metal is silver, this new treatment will have dual advantages of both antimicrobial and anti-inflammatory effects, with fewer side effects and less chance of development of resistant bacteria.

The inventors have discovered that antimicrobial metals selected from one or more of silver, gold, platinum and palladium, are effective in the treatment of inflammatory skin conditions. These antimicrobial metals are formed with atomic disorder, such that ions, clusters, atoms or molecules of the metals are released at a concentration sufficient to provide a localized antimicrobial and anti-inflammatory effect. Most preferably, the antimicrobial metals are in a nanocrystalline form, and include sufficient atomic disorder to provide an antimicrobial and anti-inflammatory effect on a sustainable basis.

Without being bound by the same, it is believed that the nanocrystalline antimicrobial metals formed with atomic disorder are capable of releasing highly active clusters of the antimicrobial metal (example clusters of $Ag^0$ or $Ag^+/Ag^0$), which are responsible for the surprisingly enhanced antimicrobial activity and the surprising presence of the anti-inflammatory activity in the treatment of inflammatory skin conditions, compared with other known antimicrobials such as silver salts (ex. silver nitrate), silver zeolites which release only $Ag^+$, or silver metal and silver oxide which have only minor solubility. Clusters are known to be small groups of atoms, ions or the like, as described by R. P. Andres et al., "Research Opportunities on Cluster and Cluster-Assembled Materials", J. Mater. Res. Vol 4, No 3, 1989, p. 704. For silver, clusters are believed to contain less than the 14 atoms of a normal face centered cubic crystal lattice form of silver.

The crystalline forms of these antimicrobial metals may be used in, or formulated from, any of the following formats:

i) coatings of the antimicrobial metals on medical grade substrates, for example, dressings, meshes, films, fibres, containers, or vials, from materials composed of for example polyethylene, high density polyethylene, polyvinylchloride, latex, silicone, cotton, rayon, polyester, nylon, cellulose, acetate, carboxymethylcellulose, alginate, chitin, chitosan and hydrofibres;

ii) powders, preferably prepared as nanocrystalline powders of the antimicrobial metals, or as nanocrystalline coatings of the antimicrobial metals on biocompatible substrates in powder form, preferably on bioabsorbable and/or hygroscopic substrates such as:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, or Naturally Derived Polymers:

Proteins: albumin, fibrin, collagen, elastin;

Polysaccharides: chitosan, alginates, hyaluronic acid; and

Biosynthetic Polyesters: 3-hydroxybutyrate polymers;

iii) occlusions or hydrated dressings, in which the dressing is impregnated with a powder or solution of the antimicrobial metals, or is used with a topical formulation of the antimicrobial metals, with such dressings for example as hydrocolloids, hydrogels, polyethylene, polyurethane, polyvinylidine, siloxane or silicone dressings;

iv) gels, formulated with nanocrystalline powders or solutions of the antimicrobial metals with such materials as carboxymethylcellulose, alginate, chitin, chitosan and hydrofibres, together with such ingredients as preservatives, pectin and viscosity enhancers;

v) creams, lotions, pastes, foams and ointments formulated with nanocrystalline powders or solutions of the antimicrobial metals, for example as emulsions or with drying emollients; and vi) liquids, formulated as solutions, dispersions, or suspensions, by dissolving nanocrystalline coatings or powders of the antimicrobial metals, for example as topical solutions, aerosols, mists, sprays, or drops.

Solutions of the antimicrobial metals lose some activity with aging and are thus either stabilized or generated fresh for administration. Alternatively, the antimicrobial metals may be packaged for convenient solution generation, for instance in a pervious membrane such as a tea bag type infuser. Other two part or two phase systems may be used in which the nanocrystalline metal is separated from the water or electrolyte solvent, for example in kit form, with the antimicrobial metal being provided in dissolving capsules, as a coating on the inside of vials or containers, on substrates such as dressing, separated by a membrane which can be perforated, or in a separate container from the carrier, in a tea bag-type infuser etc.

In the above formats, the nanocrystalline antimicrobial metals are formulated from nanocrystalline coatings or nanocrystalline powders of the nanocrystalline antimicrobial metals, or from solutions prepared by dissolving the nanoc rystalline coatings or powders therein. The formulations include a therapeutically effective amount of the coatings or powders, and most preferably, the following amounts:

| | |
|---|---|
| For coatings: | 150–3000 nm thick coatings for substrates, or thicker for forming powders (such coatings can be used to generate 0.001 to 10% by weight solutions) |
| For gels, creams etc.: | 0.01–30% by weight, more preferably 0.01–10% by weight and most preferably 0.1–5% by weight of the antimicrobial or noble metal powder |
| For liquids: | 0.001–10% by weight, more preferably 0.01 to 5% by weight and most preferably 0.1 to 1% by weight of the antimicrobial or noble metal (generated from any format, including coatings, flakes, powders). |

Concentrations of the antimicrobial species in solution will vary according to the application, formulation and subject, but will generally range from 1–5000 $\mu$g/ml, more preferably 20–3000 $\mu$g/ml, more preferably 40–800 $\mu$g/ml, and most preferably 50–500 $\mu$g/ml.

Nanocrystalline coatings of the antimicrobial metals are most preferably deposited onto substrates such as dressings, for example one or more layers of medical dressing materials which can be laminated with uncoated layers of medical dressing materials. The coatings can be prepared by known techniques for preparing nanocrystalline coatings, but are most preferably prepared by physical vapour deposition under conditions which create atomic disorder. The nanocrystalline coatings may be prepared to create an interference colour so as to provide an indicator, as described in prior patent application WO 98/41095, published Sep. 24, 1998, and naming inventors R. E. Burrell and R. J. Precht.

Nanocrystalline powders of the antimicrobial metals may be prepared as nanocrystalline coatings, preferably of the above thickness, on powdered substrates such as chitin, or may be prepared as nanocrystalline coatings on a substrate such as a silicon wafer, and then scraped off as a nanocrystalline powder. Alternatively, fine grained or nanocrystalline powders of the antimicrobial metals may be cold worked to impart atomic disorder, as taught in prior patent applications WO 93/23092, published Nov. 25, 1993, and WO 95/13704, published May 26, 1995, both of which name Burrell et al., as inventors.

Thus, the invention broadly provides a method of reducing inflammation of an inflammatory skin condition which comprises:

contacting a problem area of a patient, with a therapeutically effective amount of the antimicrobial metals in a crystalline form to provide a localized anti-inflammatory effect, wherein the antimicrobial metals are characterized by sufficient atomic disorder, such that the metal, in contact with an alcohol or water-based electrolyte, releases atoms, ions, molecules, or clusters of at least one antimicrobial metal at a concentration sufficient to provide a localized anti-inflammatory and antimicrobial effect. The antimicrobial metal is nanocrystalline and is formed with sufficient atomic disorder such that, in contact with an alcohol or water based electrolyte, the antimicrobial metal releases ions, atoms, molecules or clusters of the antimicrobial metal on a sustainable basis. The antimicrobial metal is selected from the group consisting of silver, gold, platinum and palladium, but preferably is nanocrystalline silver or silver, formed as a composite with oxygen.

In another broad aspect of the invention, there is provided a method of reducing inflammation of an inflammatory skin condition which comprises:

applying a hydrated dressing to contact a problem area of a patient, wherein the hydrated dressing i includes a therapeutically effective amount of one or more antimicrobial metals in a crystalline form to provide a localized antimicrobial and anti-inflammatory effect; or ii occludes a pharmaceutical composition of a nanocrystalline powder of the one or more antimicrobial metals, or a solution containing dissolved species from a nanocrystalline powder or coating of the one or more antimicrobial metals.

In another broad aspect, the invention provides a hydrated dressing for use in reduction of inflammation of an inflammatory skin condition comprising a hydrated dressing, and associated with the dressing, a therapeutically effective amount of one or more antimicrobial metals in a crystalline form to provide localized anti-inflammatory and antimicrobial effects.

In yet another broad aspect, the invention provides a kit for reducing inflammation of an inflammatory skin condition comprising one or more antimicrobial metals formed with atomic disorder; and one or more pharmaceutically acceptable carriers.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Antimicrobial metals" are silver, gold, platinum, palladium, iridium, zinc, copper, tin, antimony, bismuth, or mixtures of these metals with same or other metals, silver, gold, platinum and palladium being preferred, and silver being most preferred.

"Noble metals" are silver, gold, platinum and palladium, or mixtures of such metals with same or other metals, with silver metal being the most preferred.

"Antimicrobial effect" means that atoms, ions, molecules or clusters of the antimicrobial or noble metal are released into the electrolyte which the coating contacts in concentration sufficient to inhibit microbial growth on and in the vicinity of the coating. The most common methods of measuring an antimicrobial effect are a zone of inhibition test (which indicates an inhibitory effect, whether microbiostatic or microbiocidal) or a logarithmic reduction test (which indicates a microbiocidal effect). In a zone of inhibition test (ZOI) the material to be tested is placed on a bacterial lawn (or a lawn of other microbial species) and incubated. A relatively small or no ZOI (ex. less than 1 mm) indicates a non-useful antimicrobial effect, while a larger ZOI (ex. greater than 5 mm) indicates a highly useful antimicrobial effect. The ZOI is generally reported as a corrected zone of inhibition (CZOI), wherein the size of the test sample is subtracted from the zone. A logarithmic reduction test in viable bacteria is a quantitative measure of the efficacy of an antibacterial treatment; for example, a 5 log reduction means a reduction in the number of microorganisms by 100,000-fold (e.g., if a product contained 100,000 pertinent microorganisms, a 5 log reduction would reduce the number of pertinent microorganisms to 1). Generally, a 3 log reduction represents a bactericidal effect. The logarithmic reduction test involves combining the inoculum with the test treatment, incubating the inoculum with the test treatment, recovering the bacteria or other microbial species, and enumerating the bacteria or other microbial species using serial dilutions. Examples of these tests are set out in the examples which follow.

"Anti-inflammatory effect" means a reduction in one or more of the symptoms of erythema (redness), edema (swelling), pain and pruritus which are characteristic of inflammatory skin conditions.

"Inflammatory skin conditions" refers to those conditions of the skin in which inflammatory cells (e.g., polymorphonuclear neutrophils and lymphocytes) infiltrate the skin with no overt or known infectious etiology, but excluding psoriasis and its related conditions. Symptoms of inflammatory skin conditions generally include erythema (redness), edema (swelling), pain, pruritus, increased surface temperature and loss of function. As used herein, inflammatory skin conditions include, but are not limited to, eczema and related conditions, insect bites, erythroderma, mycosis fungoides and related conditions, pyoderma gangrenosum, erythema multiforme, rosacea, onychomycosis, and acne and related conditions, but excluding psoriasis and its related conditions.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of an antimicrobial metal that continues over time measured in hours or days, and thus distinguishes release of such metal species from the bulk metal, which release such species at a rate and concentration which is too low to be therapeutically effective, and from highly soluble salts of antimicrobial metals such as silver nitrate, which releases silver ions virtually instantly, but not continuously, in contact with an alcohol or electrolyte.

"Atomic disorder" includes high concentrations of one or more of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the antimicrobial materials of the present invention might contact in order to activate (i.e. cause the release of species of the antimicrobial metal) into same. The term is meant to include alcohols (short chain ($C_6$ or less) and preferably $C_4$ or less), water, gels, fluids, solvents, and tissues containing, secreting, or exuding water or water-based electrolytes, including body fluids (for example blood, urine, or saliva), and body tissue (for example skin).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the antimicrobial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Pharmaceutically- or therapeutically-acceptable" is used herein to denote a substance which does not significantly interfere with the effectiveness or the biological activity of the active ingredients (antimicrobial and anti-inflammatory activities) and which has an acceptable toxic profile for the host to which it is administered.

"Therapeutically effective amount" is used herein to denote any amount of a formulation of the antimicrobial or noble metals which will exhibit either or both of an antimicrobial and optionally an anti-inflammatory effect, when applied to the affected area of the skin. A single application of the formulations of the present invention may be sufficient, or the formulations may be applied repeatedly over a period of time, such as several times a day for a period of days or weeks. The amount of the active ingredient, that is the antimicrobial or noble metal in the form of a coating, powder or dissolved in liquid solution, will vary with the conditions being treated, the stage of advancement of the condition, the age and type of host, and the type and concentration of the formulation being applied. Appropriate amounts in any given instance will be readily apparent to those skilled in the art or capable of determination by routine experimentation.

"Carrier" means a suitable vehicle including one or more solid, semisolid or liquid diluents, excipients or encapsulating substances which are suitable for administration to the skin.

"Nanocrystalline" is used herein to denote single-phase or multi-phase polycrystals, the grain size of which is less than about 100, more preferably <50, even more preferably <40, even more preferably <30, and most preferably <25 nanometers in at least one dimension. The term, as applied to the crystallite or grain size in the crystal lattice of coatings, powders or flakes of the antimicrobial or noble metals, is not meant to restrict the particle size of the materials when used in a powder form.

"Powder" is used herein to include particulates of the antimicrobial or noble metals ranging from nanocrystalline (less than 100 nm) to submicron sized powders up to flakes. Preferably, powders of the antimicrobial or noble metals used in the present invention are sized at less than 100 $\mu$m, and more preferably less than 40 $\mu$m, and most preferably less than 10 $\mu$m.

"Grain size", or "crystallite size" means the size of the largest dimension of the crystals in the antimicrobial metal coating or powder.

"Hydrocolloid" means a synthetically prepared or naturally occurring polymer capable of forming a thickened gel in the presence of water and polyols (swelling agent). The swelling agent must be capable of swelling the hydrocolloid chosen in order to form the gel phase.

"Hydrogels" means a hydrocolloid swollen with water or another hydrophilic liquid which is used for absorbing or retaining moisture or water.

"Gel" means a composition that is of suitable viscosity for such purposes, e.g., a composition that is of a viscosity that enables it to be applied and remain on the skin.

When used herein and in the claims, the term "nanocrystalline antimicrobial metal" and similar terminology, such as "nanocrystalline coatings or powders" is meant to refer to antimicrobial metals formed with atomic disorder and having a nanocrystalline grain size.

DESCRIPTION OF THE PREFERRED EMBODIMENTS

Figure 1:
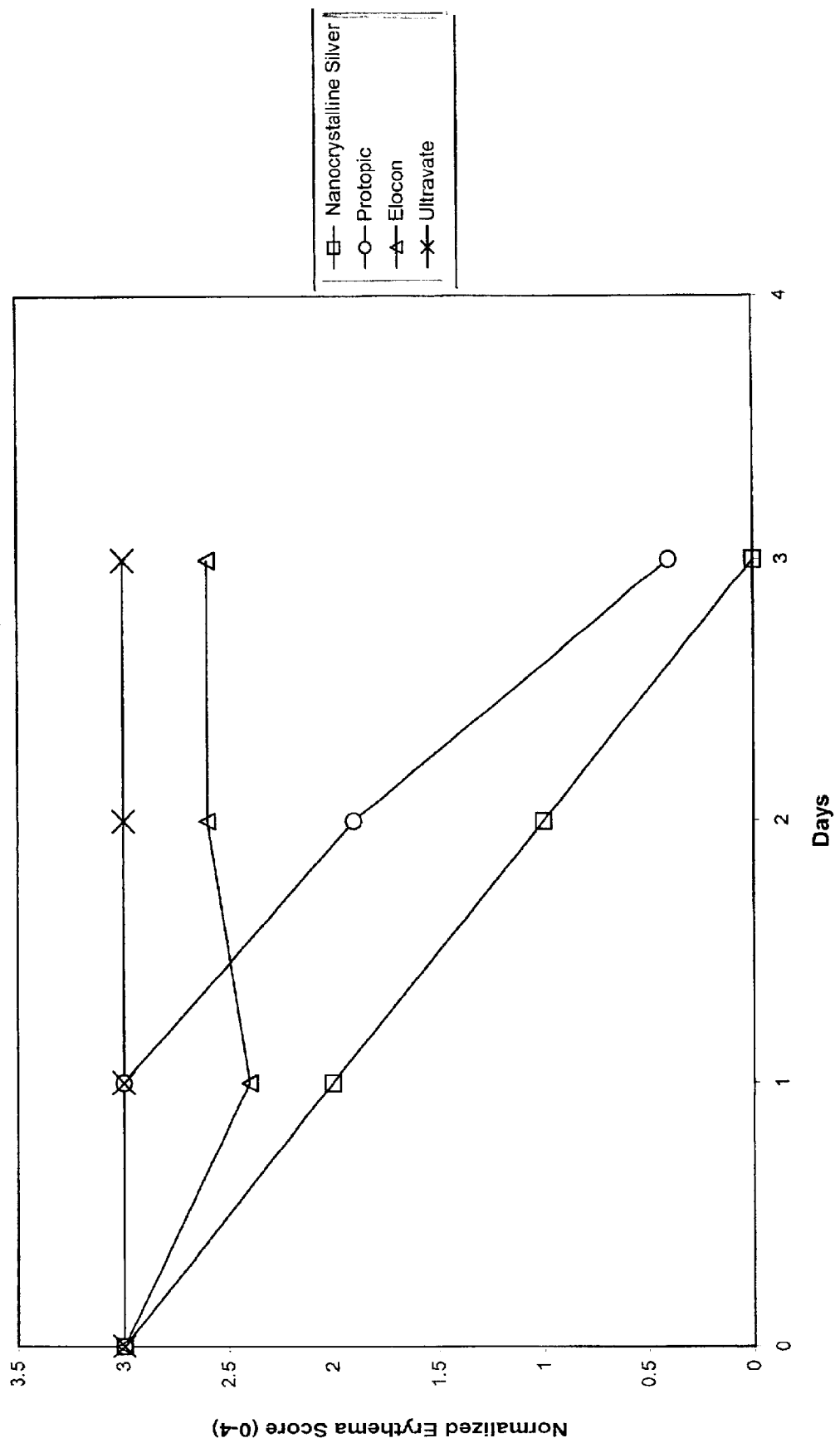
FIG. 1 is a graph showing the efficacy of the nanocrystalline silver powder compared to Protopic™ or tacrolimus (non-steroidal anti-inflammatory), Elocon™ (medium strength steroid) and Ultravate™ (high strength steroid), on erythema.

Crystalline forms of the antimicrobial metals can be prepared as coatings or powders, or as solutions prepared by dissolving the coatings or powders. The crystalline coatings or powders are most preferably formed with atomic disorder in accordance with the techniques published in the prior patent applications of Burrell et al., see for example WO 93/23092, published Nov. 25, 1993, WO 95/13704, published May 26, 1995 and WO 98/41095, published Sep. 24, 1998.

Pharmaceutical formulations for treatment of inflammatory skin conditions utilize the antimicrobial metals in powder, coatings or solution form. Preparation of the antimicrobial metals as powders or coatings is set out below in section A, format for formulations are set forth in section B, sterilization in section C, and formulating, dosages and treatment are set forth in section D.

A. Preparation of Crystalline Forms of the Antimicrobial Metals with Atomic Disorder a) Antimicrobial Metal Coatings on Dressings or Other Substrates Dressings or other substrates such as packings, vials, fabric, fibres etc. may be coated with antimicrobial coatings formed with atomic disorder. The description below is directed to coatings on dressing materials, but the coating techniques are equally applicable to coating other substrates. Dressings coated with antimicrobial metals in accordance with the invention include one or more layers of medical dressing materials. Multiple layers may be laminated together by known means such as low temperature thermal fusing, stitching or, most preferably, ultrasonic welding.

The dressing may be formed to include an occlusive or semi-occlusive layer such as an adhesive tape or polyurethane film in order to secure the dressing in place, and retain moisture for release of ions, atoms, molecules or clusters of the antimicrobial metal (hereinafter antimicrobial metal species).

The preferred and alternate compositions of the dressing layers, together with the preferred nanocrystalline antimicrobial metal coatings, are set out in further detail below.

i) Dressing Materials

The dressing is formed of a perforated, preferably non-adherent material which allows for fluids to penetrate or diffuse there through in either or both directions. The perforated material may be formed of a woven or non-woven, non-woven being preferred, fabric such as cotton, gauze, a polymeric net or mesh such as polyethylene, nylon, polypropylene or polyester, an elastomer such as polyurethane or polybutadiene elastomers, or a foam such as open cell polyurethane foam. Exemplary perforated, non-adherent materials useful for the dressing include non-woven meshes such as DELNET™ P530, which is a non-woven veil formed of high density polyethylene using extrusion, embossing and orientation processes, produced by Applied Extrusion Technologies, Inc. of Middletown, Del., USA. This same product is available as Exu-Dry CONFORMANT 2™ Wound Veil, from Frass Survival Systems, Inc., Bronx, N.Y., USA as a subset of that company's Wound Dressing Roll (Non-Adherent) products. Other useful non-woven meshes include CARELLE™ or NYLON 90™, available from Carolina Formed Fabrics Corp., N-TERFACE™, available from Winfield Laboratories, Inc., of Richardson, Tex., USA. Exemplary woven meshes may be formed from fibreglass or acetate, or cotton gauze. An exemplary hydrophilic polyurethane foam is HYPOL™, available from W. R. Grace & Co., New York, N.Y., USA.

For ease of ultrasonic welding for lamination, at least one dressing layer is preferably formed from a polymeric material which is amenable to ultrasonic welding, that is which will melt on the application of localized heat and then fuse multiple layers together on cooling.

If desired, a second, absorbent layer is formed from an absorbent material for holding sufficient moisture next to the skin in order to activate the antimicrobial metal coating, that is to cause release of ions, molecules, atoms or clusters of the antimicrobial metal in order to cause an antimicrobial and anti-inflammatory effect. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers such as rayon, polyester, rayon/polyester, polyester/cotton, cotton and cellulosic fibers. Exemplary are creped cellulose wadding, an air felt of air laid pulp fibers, cotton, gauze, and other well known absorbent materials suitable for medical dressings.

A third layer of the dressing, if used, is preferably formed of perforated, non-adherent material such as used in the first layer. This allows moisture penetration as sterile water and the like are added in order to activate the antimicrobial metal coating.

Additional layers may be included between or above the first, second and third layers as is well known in medical dressings. The coated dressing layers may be combined with an adhesive layer, in a well known manner.

The dressing may be used as a single layer, or may be used as multiple layers laminated together at intermittent spaced locations across the dressing by ultrasonic welds. Ultrasonic welding is a known technique in the quilting art. Briefly, heat (generated ultrasonically) and pressure are applied to either side of the dressing at localized spots through an ultrasonic horn so as to cause flowing of at least one of the plastic materials in the first and second layers and the subsequent bonding together of the layers on cooling. The welds appear at localized circular spots and are preferably less than 0.5 cm in diameter.

The use of ultrasonic welding of the layers at spaced locations has the advantage of retaining the absorbent and moisture penetration properties of the dressing layers, while retaining the conforming properties of the dressing. Edge seams, stitching and adhesives have the disadvantage of interfering with one or more of these desirable properties of the is dressings. Furthermore, by spacing the welds at intermittent locations across the dressing, the dressing may be cut to smaller sizes, as needed, without causing delamination. Preferred spacings of about 2.5 cm between welds allows the dressing to be cut down to about 2.5 cm sizes, while maintaining at least one weld to hold the laminated layers together.

ii) Nanocrystalline Coatings of Antimicrobial Metals

The coated substrate, for example a dressing, preferably includes a nanocrystalline coating of one or more of the antimicrobial metals. The coating is applied to one or more of the dressing layers, but is most preferably applied at least to the skin facing layer.

The nanocrystalline coating is most preferably formed with atomic disorder in accordance with the procedures set out above and as described in WO 93/23092, WO 95/13704, and WO98/41095, and as set out below. Most preferably, the coating is formed as a multilayer coating of the antimicrobial metals, having a top and a base layer, as set below, to produce an interference colour. In this way, the coating provides not only the active ingredient for the treatment of inflammatory skin conditions, but also acts as an indicator of activation of the dressing. As the top layer of the coating is activated with an alcohol or water-based electrolyte, such as sterile water or ethanol, even minor dissolution of the antimicrobial metal results in a detectable colour change, indicating that the coating has been activated. If there is no colour change, additional moisture might be provided to the dressing by adding water, until a colour change is detected. Once activated, the dressing should be maintained in a moist condition, for example by the addition of sterile water, if necessary.

iii) Multilayer Nanocrystalline Coatings of Antimicrobial Metals With Interference Colour The coated substrates, for example dressings may include the antimicrobial metal coating formed with at least two metal layers, a base layer and a top layer over the base layer, so as to produce an interference colour, as set forth in WO 98/41095, the teachings of which are incorporated herewith by reference. The indicator colour can function as an indicator when contacted with a water or alcohol based electrolyte, since the coating will change colour. An exemplary multilayer nanocrystalline coating of silver with a blue interference colour is set forth in Example 1.

iv) Nanocrystalline Coatings of Antimicrobial Metals Containing Atomic Disorder

The coatings of the present invention are formed in a crystalline form from one or more antimicrobial metals with atomic disorder. The production of atomic disorder through physical vapour deposition techniques is described in WO 93/23092 and WO 95/13704, and as outlined below.

The antimicrobial metal is deposited as a thin metallic film on one or more surfaces of the dressing by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, "Influence of Apparatus Geometry and Deposition Conditions on the Structure and Topography of Thick Sputtered Coatings," J. Vac. Sci. Technol., 11(4), 666–670, 1974).

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working gas pressure (or ambient pressure in depositions not using a working gas), i.e. for vacuum evaporation: e-beam or arc evaporation, greater than 0.001 Pa (0.01 mT), gas scattering evaporation (pressure plating) or reactive arc evaporation, greater than 2.67 Pa (20 mT); for sputtering: greater than 10 Pa (75 mT); for magnetron sputtering: greater than about 1.33 Pa (10 mT); and for ion plating: greater than about 26.67 Pa (200 mT); and maintaining the angle of incidence of the coating flux on the surface to be coated at less than about 75°, and preferably less than about 30°.

For economic reasons, the thin metal film has a thickness no greater than that needed to provide release of antimicrobial metal species on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The therapeutic effect of the material so produced is achieved when the coating is brought into contact with an alcohol or a water based electrolyte, thus releasing metal ions, atoms, molecules or clusters. The concentration of the metal species which is needed to produce a therapeutic effect will vary from metal to metal.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at T/Tm<0.5 and a working gas pressure of about 0.93 Pa (7 mT) releases approximately ⅓ of the silver ions that a film deposited under similar conditions, but at 4 Pa (30 mT), will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 2 Pa or 15 mT) for 50% of the deposition time and high (ex. 4 Pa or 30 mTorr) for the remaining time, has a rapid initial release of metal ions, followed by a longer period of slow release. This type of coating is extremely effective on devices such as urinary catheters for which an initial rapid release is required to achieve immediate antimicrobial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable $\Delta T$, that the temperature differential between the substrate temperature during deposition and the ultimate temperature of use, will vary from metal to metal. For the most preferred metal, Ag, preferred substrate temperatures of −20 to 200° C., more preferably −10° C. to 100° C. are used.

Atomic order may also be achieved, in either or both of the base and top layers by preparing composite metal materials, that is materials which contain one or more antimicrobial metals in a metal matrix which includes atoms or molecules different from the antimicrobial metals.

The preferred technique for preparing a composite material is to co- or sequentially deposit the antimicrobial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial metals, which results in atomic disorder during deposition. Alloys of this kind can also serve to reduce atomic diffusion and thus stabilize the disordered structure. Thin film deposition equipment with multiple targets for the placement of each of the antimicrobial and biocompatible metals is preferably utilized. When layers are sequentially deposited the layer(s) of the biocompatible metal(s) should be discontinuous, for example as islands within the antimicrobial metal matrix. The final weight ratio of the antimicrobial metal(s) to biocompatible metal(s) should be greater than about 0.2. The most preferable biocompatible metals are Ti, Ta, Zn and Nb. It is also possible to form the antimicrobial coating from oxides, carbides, nitrides, sulphides, borides, halides or hydrides of one or more of the antimicrobial metals and/or one or more of the biocompatible metals to achieve the desired atomic disorder.

Another composite material may be formed by reactively co- or sequentially depositing, by physical vapour techniques, a reacted material into the thin film of the antimicrobial metal(s). The reacted material is an oxide, nitride, carbide, boride, sulphide, hydride or halide of the antimicrobial and/or biocompatible metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final weight ratio of reaction product to antimicrobial metal (s) should be greater than about 0.05. Air, oxygen, nitrogen and hydrogen are particularly preferred reactants, with oxygen being most preferred.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

The most preferred composite coatings are formed by sputtering silver, under conditions set out above, in an atmosphere containing oxygen, so as to form a coating of silver as a composite coating with oxygen.

Dressings coated with the antimicrobial coatings of this invention may be sterilized in the manner set out below.

b) Powders of Atomically Disordered Antimicrobial Metals

Crystalline powder forms of the antimicrobial or noble metals particularly preferred being Ag, Au, Pt, and Pd) can be prepared as free standing powders, by coating powdered substrates, or from coatings on substrates which are then collected, for example by scaping and then sized. The powders may be prepared as pure metals, metal alloys or compounds such as metal oxides or metal salts, by vapour deposition, mechanical working, or compressing to impart the atomic disorder. The crystalline powders are formed with atomic disorder in accordance with the techniques set out above and as published in the prior patent applications of Burrell et al., see for example WO 93/23092, published Nov. 25, 1993, and WO 95/13704, published May 26, 1995. The atomic disorder will most typically be formed in the metal powders during physical vapour deposition as set out above for coatings or by mechanically imparting the disorder, such as by milling, grinding, hammering, mortar and pestle or compressing, under conditions of low temperature (i.e., temperatures less than the temperature of recrystallization of the material) to ensure that annealing or recyrstallization does not take place.

Alternatively, the powders may be formed by inert-gas condensation techniques, which are modified to provide atomic disorder in the powder produced, as taught in WO 95/13704 to Burrell et al.

Powders of the antimicrobial or noble metals are preferably formed by physical vapour deposition (PVD) onto a substrate such as a cold finger, a silicon wafer, solid plates, a rotating cylinder, a continuous belt in a roll coater, or on steel collectors in known PVD coaters. Preparation of powders of the present invention by sputtering onto a continuous belt in a roll coater, or other some other moving or rotating substrate surface is particularly advantageous, inasmuch as it can quickly and easily yield a relatively large supply of free-standing powder at a relatively low cost. A stainless steel belt can be used in the roll coating process without the need to provide additional cooling of the substrate. The powders or coatings and then are then scraped off to form a powder, and may be sized to avoid overly large particulates. The powders are scraped off the moving surface with scrapers which contact the moving surface at an angle sufficient to remove the coating in flake or powder form. The coating may be scraped off with scrapers angled for forward cutting of the coating from the moving surface, or with scrapers which remove the coating from the moving surface by reverse dragging action on the surface. The scrapers may be suspended above the belt, and either weighted or spring loaded to apply pressure sufficient to remove the coating from the moving surface. With a continuous belt, the scrapers can conveniently be located above the end rollers to remove the coating with a reverse dragging action as the belt rounds the end roller.

Alternatively, the powders of the antimicrobial or noble metals may be formed on powdered substrates which are biocompatible, or otherwise compatible for the end use of the powder. Particularly preferred powdered substrates are hydrocolloids, particularly those which are bioabsorbable and/or hygroscopic powders such as chitin. Exemplary bioabsorbable and/or hygroscopic powders are composed of Synthetic Bioabsorbable Polymers: for example polyesters/
polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers:
Proteins: albumin, fibrin, collagen, elastin;
Polysaccharides: chitosan, alginates, hyaluronic acid; and
Biosynthetic Polyesters: 3-hydroxybutyrate polymers.

The powders may be incorporated into or onto medical dressings or pharmaceutical formulations, by any methods known in the art. For example, the powders may be layered onto the substrates (dressings or powders), mechanically fixed within the fibres of the dressings, impregnated into dressings by physical blowing, or added to topical pharmaceutical ingredients.

Preferably, powders of the present invention are sized at less than 100 $\mu$m, and more preferably less than 40 $\mu$m, and most preferably about 3–5 $\mu$m in size. For direct application to the skin, powders are preferably sized less than 2 $\mu$m, and more preferably less than 1 $\mu$m.

B. Formulations for Administration to the Skin

1. Coated substrates coated with antimicrobial metals formed with atomic disorder are well described above. These techniques can be used to coat dressings, meshes, films, packing fibres, the insides of vials or containers etc. The coated substrates in the form of dressings for example, can be used directly on the affected area of the skin, or they can be used to generate powders, liquid or other formulations as set out below.

2. Powders of the antimicrobial metals formed with atomic disorder are set out above, and may be used in that form directly on the affected area of the skin, or in other formulations such as dressings, occlusions, creams, liquids etc. Alternatively, powders may be formulated within liquid pervious membranes such as filters, meshes and the like, such as a tea bag-type infuser, for generating liquids containing dissolved species of the antimicrobial metal.

3. Occlusions may include a hydrated dressing, with a sealing material overlaid on the outside, to the area of skin to be treated. The term hydrated dressing is meant to include non-hydrated dressings which become hydrated upon contact with an alcohol or water-based electrolyte. Occlusion prevents loss of the therapeutic agent from the skin, promotes skin hydration, and increases skin temperature. Examples of hydrated dressings include hydrocolloids, hydrogels, polyethylene, polyurethane, polyvinylidine, and siloxane or silicone dressings. A hydrated dressing may also comprise a non-hydrated dressing which becomes hydrated upon contact with an alcohol or water-based electrolyte. The hydrated dressing can either be impregnated with a solution or powder of the antimicrobial metals of this invention, or can be used with a topical formulation of the antimicrobial metals of this invention.

An exemplary occlusion is a hydrocolloid dressing impregnated with nanocrystalline silver. Alternatively, one might use a non-impregnated hydrocolloid dressing to occlude a nanocrystalline silver-containing gel placed on a problematic area of the skin. A hydrocolloid is a synthetically prepared or naturally occurring polymer capable of forming a thickened gel in the presence of water and polyols (swelling agent). The swelling agent is a hydrophilic liquid capable of swelling the hydrocolloid chosen in order to form the gel phase. The hydrocolloid may be selected from the group comprising:

i representative natural or synthetically modified polysaccharides (e.g., cellulose or its derivatives such as carboxymethylcellulose, hydroxypropylcellulose, methylcellulose, hydroxypropylmethylcellulose or hydroxyethylcellulose, starch, glycogen, gelatin, pectin, chitosan and chitin; and ii representative gums from algal extracts, seed extracts, or plant exudates (e.g., gum arabic, locust bean gum, karaya gum, gum tragacanth, ghatti gum, agar-agar, carrageenans, alginates, carob gum, guar gum, xanthan gum); and iii synthetic polymers which may be either linear or crosslinked (e.g. polymers prepared from N-vinyl lactams, e.g. N-vinyl-2-pyrrolidone, 5-methyl-N-vinyl-2-pyrrolidone).

The hydrocolloid is present in an amount of from about 0.1% to 20% of the weight and preferably 1% to 10%. The hydrocolloid can range for example, from 1 to 10% of the total weight of the composition. Alternatively, the hydrocolloid may be in the form of a powder whose average particle size is less than 100 $\mu$m, preferably less than 50 $\mu$m.

The swelling agent should be non-volatile, and allow the gel to remain as a gel during use, hence preserving the swollen condition of the hydrocolloid. Varieties of non-volatile swelling agents include room temperature liquid polyols (including polyhydric alcohols) such as glycerol; room temperature solid polyols (including polyhydric alcohols) such as sorbitol, erythritol, threitol, ribotol, arabinitol, xylitol, allitol, talitol, mannitol, glucitol, glactitol, iditol, pentaerythritol, heptitol, octitol, nonitol, decitol, and dodecitol, blended with a room temperature liquid polyol; monoanhydroalditols (such as styracitol, polyalitol, D-fructose, 1,4 anhydro-D-mannitol and 1,4 anhydro-D-glucitol) blended with a room temperature liquid polyol; monosaccharides (such as pentoses, hexoses, and heptoses) blended with a room temperature liquid polyol; and ether alcohols blended with a room temperature liquid polyol.

Hydrocolloid dressings often comprise a wafer constructed from a thin layer of polyurethane film with an adhesive skin contact layer containing a hydrocolloid composition and securing the dressing to the skin, and the polyurethane film being impermeable to water and microorganisms. Hydrocolloid dressings may be prepared by dispersing a composition in gel form of hydrocolloids with a swelling agent into a strong pressure sensitive adhesive. Alternatively, the gel and the adhesive may be mixed in a latex solution. Alternatively, exemplary products are available commercially, for example DuoDERM™ (ConvaTec Canada, 555, Dr. Frederik Philips, Suite 110, St-Laurent, Quebec, H4M 2X4); and Tegasorb™ (3M Health Care, 300 Tartan Drive, London, Ontario, Canada, N5V 4M9). The hydrocolloid dressing may be impregnated with a solution or powder of the antimicrobial metals by blending the solution or powder of the antimicrobial metal into a liquid phase during the manufacture of the hydrocolloid dressing, or by sprinkling and then pressing a powder of the antimicrobial metal into the surface of the hydrocolloid dressing. Further, the hydrocolloid dressing can be used with a topical formulation of the antimicrobial metals of this invention. Upon application, the dressing surface gels upon continued contact with moisture or exudate from the skin. With the incorporation of an antimicrobial metal such as silver (0.01–10%, preferably 0.1–1% by weight), the dressing is advantageous in being impermeable to water and microorganisms, and presenting antimicrobial and anti-inflammatory effects as mediated by the antimicrobial metal.

4. Gels—Nanocrystalline gels may be formed from the nanocrystalline metal powder in admixture with gelling agents such as hydrocolloids and hydrogels in powder form. Exemplary gelling agents include carboxymethyl cellulose (CMC), polyvinyl alcohol (PVA), collagen, pectin, gelatin, agarose, chitin, chitosan, and alginate, with the gelling agent comprising between about 0.01–20% w/v. Examples of gel preparations are set out in Example 11. Example 12 demonstrates the use of a nanocrystalline silver gel preparation as set forth in Example 11, with a non-impregnated hydrocolloid dressing to occlude the nanocrystalline silver gel placed on a problematic area of the skin.

5. Creams, Lotions, Pastes, Ointments, Foams—The antimicrobial metals may be incorporated into creams, lotions, pastes, ointments or foams formulated with nanocrystalline powders or solutions of the antimicrobial metals, for example as emulsions or with drying emollients. Ointments and creams can be formulated with an aqueous or oily base with the addition of suitable thickening and/or gelling agents. Such bases may include water and/or an oil such as liquid paraffin or a vegetable oil such as peanut oil or castor oil. An exemplary base is water. Thickening agents which can be used according to the nature of the base include aluminum stearate, hydrogenated lanolin, and the like. Further, lotions can be formulated with an aqueous base and will, in general, also include one or more of the following: stabilizing agents, emulsifying agents, dispersing agents, suspending agents, thickening agents, coloring agents, perfumes, and the like. Ointments and creams can also contain excipients, such as starch, tragacanth, cellulose derivatives, polyethylene glycols, silicones, bentonites, silicic acid, and talc, or mixtures thereof. Lotions may be formulated with an aqueous or oily base and will, in general, also include one or more of the following: stabilizing agents, emulsifying agents, dispersing agents, suspending agents, thickening agents, coloring agents, perfumes, and the like. Foams may be formed with known foaming or surface active agents.

6. Liquids—The crystalline forms of the antimicrobial metals may be incorporated into liquids, formulated as solutions, dispersions or suspensions by dissolving nanocrystalline coatings or powders of the antimicrobial metals, for example as topical solutions, aerosols, mists, sprays, or drops. Topical administration of the antimicrobial metal to the skin may be performed by aerosol, which can be generated by a nebulizer, or by instillation. The antimicrobial metal may be administered alone, or with a carrier such as saline solution, an alcohol, water, or DMSO. An effective daily amount of the antimicrobial metal will vary with the subject, but will be less than is toxic while still providing a therapeutic effect.

Solutions and formulations of the antimicrobial metals may lose some activity with aging and are thus either stabilized or generated fresh for administration. Alternatively, the antimicrobial metals may be packaged for convenient solution generation, for instance as tea bag type infusers. Other two part or two phase systems may be used in which the nanocrystalline metal is separated from the water or alcohol-based electrolyte, for example in a multi-component kit form, as set out herein.

Concentrations of the antimicrobial metal species in solution will vary according to the application, formulation and subject, but will generally range from 1–5000 $\mu$g/ml, more preferably 20–3000 $\mu$g/ml, more preferably 40–800 $\mu$g/ml, and most preferably 50–500 $\mu$g/ml. Methods of generating liquids with appropriate concentrations of the antimicrobial metal through pH control are set out below.

7. Transdermal Patch

Transdermal patches may provide controlled delivery of the antimicrobial metal to the skin. For example, an adhesive patch or adhesive matrix patch, can be prepared from a backing material and an adhesive, such as an acrylate adhesive. Powders or solutions of the antimicrobial metal may be formulated into the adhesive casting solution and allowed to mix thoroughly. The solution is cast directly onto the backing material and the casting solvent is evaporated in an oven, leaving an adhesive film. Alternatively, a polyurethane matrix patch can be employed to deliver the antimicrobial metal to the skin. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and drug to the prepolymer results in the formation of a tacky firm elastomer that can be directly cast onto the backing material.

C. Sterilization

Dressings with nanocrystalline coatings of a antimicrobial metal formed with atomic disorder are preferably sterilized without applying excessive thermal energy, which can anneal out the atomic disorder, thereby reducing or eliminating a useful release of antimicrobial metal species. Gamma radiation is preferred for sterilizing such dressings, as discussed in WO 95/13704. Electron beam and ethylene oxide sterilization techniques can also be used.

It should be appreciated that the use of ultrasonic welding to laminate the layers of dressings with nanocrystalline coatings formed from antimicrobial metals with atomic disorder is advantageous since it achieves bonding in localized spots and avoids applying heat to any significant portion of the dressing, thereby avoiding any significant reduction in the solubility of the antimicrobial metals through annealing out of the atomic disorder.

The sterilized dressings, coating, powders or formulations should be sealed in packaging, containers, or kits which limit moisture and light penetration to avoid additional oxidation or reduction of the antimicrobial metal. Polyester peelable pouches are preferred. The shelf life of coatings or powders thus sealed is over one year.

D. Formulating, Dosages and Treatment

Typically, the nanocrystalline antimicrobial metals will be formulated from the active ingredient, namely nanocrystalline powders or coatings of the antimicrobial metals, or dissolved species from such powders or coatings, in the one or more of the formats set out above. Dressing or powders of the nanocrystalline antimicrobial metals may be applied directly to the skin, or they may be formulated as set out below. Depending on the particular application and dosage form, the powder size might be controlled to less than 2 $\mu$m, more preferably to less than 1 $\mu$m.

In the pharmaceutical compositions, the amount of the nanocrystalline metal powder may range broadly from about 0.001% to about 30% by weight, but will more preferably fall in the range of from about 0.1 to 10% by weight, and most preferably in the range of about 0.01 to 5% by weight. Typical coating thicknesses are in the range of 150 to 3000 nm thick. Thicker coatings, up to 10,000 nm thick, can be used to generate powders of the antimicrobial metal. Coatings of the nanocrystalline antimicrobial metals may be very thin, or thick, depending on the desired duration of application on the patient. As liquid formulations, the amount of dissolved antimicrobial metal will typically range between about 0.001 to 10% by weight, more preferably 0.01 to 1% by weight.

Besides the active ingredient, pharmaceutical compositions may also include non-toxic, pharmaceutically acceptable carriers, diluents and excipients, suitable for topical application, as are well known, see for example Merck Index, Merck & Co., Rahway, N.J.; and Gilman et al., (eds) (1996) Goodman and Gilman's: The Pharmacological Bases of Therapeutics, $8^{th}$ Ed., Pergamon Press. For standard dosages of conventional pharmacological agents, see, e.g., Physicians Desk Reference (1997 Edition); and U.S. Pharmacopeia National Formulary (1995) United States Pharmacopeial Convention Inc., Rockville, Md.

Dosage forms for the topical administration of compositions of the nanocrystalline antimicrobial metals include various mixtures and combinations that can be applied topically and will permit even spreading and absorption into the cutaneous surfaces. Examples include sprays, mists, aerosols, lotions, creams, solutions, gels, ointments, pastes, emulsions, foams and suspensions. The active compound can be mixed under sterile conditions with a pharmaceutically acceptable carrier, and with any preservatives, buffers, or propellants which may be required. Topical preparations can be prepared by combining the antimicrobial metal powder with conventional pharmaceutically acceptable carriers commonly used in topical dry, liquid, cream and aerosol formulations. For example, in cases of distal and/or lateral subungual onychomycosis and proximal subungual onychomycosis, infection may extend under the nail plate; thus, topical formulations such as a liquid, solid, or gel must thus be able to pass through the hard nail plate in order to contact the affected area. The affected nail can be initially hydrated using urea (1–40%) or lactic acid (10–15%), and then treated with the antimicrobial metal (0.1–2%, more preferably 0.1–1%) in DMSO (0.4–50%), a carrier which can infiltrate the nail.

Ointment and creams can, for example, be formulated with an aqueous or oily base with the addition of suitable thickening and/or gelling agents. An exemplary base is water. Thickening agents can be used according to the nature of the base. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose starch and the like. Drops can be formulated with an aqueous base or non-aqueous base, and can also include one or more dispersing agents, suspending agents, solubilizing agents, surface active agents and the like.

Ointments, pastes, creams and gels also can contain excipients, such as starch, tragacanth, cellulose derivatives, silicones, bentonites, silicic acid, and talc, or mixtures thereof. Powders and sprays also can contain excipients such as lactose, talc, silicic acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such inert gases such as nitrogen, carbon dioxide, argon or neon.

Multiple inactive ingredients are generally incorporated in topical formulations to improve cosmetic acceptability, and are optional ingredients in the formulations. Such ingredients are included only in therapeutically acceptable forms and amounts. Examples of ingredients are emulsifiers, emollients, thickening agents, solvents, hydrating or swelling agents, flavours, sweetening agents, surface active agents, colouring agents, anti-foaming agents, preservatives, fragrances, and fillers may also be added, as is well known in the art; for example, preservatives such as methyl paraben and propyl paraben, texturizing agents, thickeners, anticoagulants such as heparin, β-glucan, hormones, hyaluronic acid, immune potentiating agents such as adjuvants and cytokines such as epidermal growth factor, platelet derived growth factor, transforming growth factor and interleukins, and bone morphogenetic proteins, and the like. Polyvinyl alcohol is a particularly preferred gelling polymer and also acts as a texturizing agent, methyl or propyl parabens are particularly preferred preservatives. These other agents may be included in amounts in the range of 0.1 to 5 wt %.

Surface active agents or foaming agents may be added to the formulations and are particularly advantageous for addition to liquid formulations for use as skin cleansers or for aerosol or foam applications. Surface active agents selected for use should not substantially interfere with the antimicrobial or anti-inflammatory effects of the nanocrystalline antimicrobial metals.

All agents must be non-toxic and physiologically acceptable for the intended purpose, and must not substantially interfere with the activity of the nanocrystalline antimicrobial metals so as to deleteriously affect the antimicrobial and anti-inflammatory effect. Ingredients are thus only included in therapeutically acceptable amounts. Ingredients to be generally avoided or limited in the formulations of the present invention, at least in amounts greater than 0.01 wt %, are glycerin, glycerols, chloride salts, aldehydes, ketones, long chain alcohols, and triethanolamine.

The dosage of the active ingredients depends upon many factors that are well known to those skilled in the art, for example, the particular form of the active ingredient, the condition being treated, the age, weight, and clinical condition of the recipient patient, and the experience and judgement of the clinician or practitioner administering the therapy. A therapeutically effective amount of the nanocrystalline antimicrobial metal provides either subjective relief of symptoms or an objectively identifiable improvement as noted by the clinician or other qualified observer. The dosing range varies with the metal used, its form, the route of administration and the potency of the particular compound.

When the formulation is in the form of a dressing, the dressing is placed on the affected area of the skin and, depending on the degree of moisture at the membrane, may be further moistened with drops of sterile water, tap water, body fluids such as exudate, or, for example 70% ethanol, in order to activate the coating for release of antimicrobial or noble metal species. The dressing may be then secured in place with an occlusive or semi-occlusive layer, such as an adhesive tape or polyurethane film, which keeps the dressing in a moist environment.

As set out in Examples 6 and 7 for acne, and Example 9 for eczema, dressings carrying a bi-layer nanocrystalline antimicrobial metal coating formed with silver having atomic disorder, manufactured as set out above and as described in greater detail in Example 1, have shown substantial clinical response in treating inflammatory skin conditions. Dressings prepared with a single layer of silver having a reduced content of oxygen in the coating, as set forth in Example 5, gave similar clinical results, without staining the skin. In use, the dressings are kept moist, at 100% relative humidity. Adding sterile water initially to activate the antimicrobial metal coating is needed, and then as needed to maintain the dressing in a moist condition. Dressings may be changed as required for observation and cleaning. Preferably dressings are changed daily, but could be left longer, such as 3 days, and can provide a therapeutic effect for a much longer period of time.

Other forms of formulations, such as occlusions, gels, pastes, ointments, creams, emulsions, foams, and liquids may be prepared in stable forms, or more preferably are prepared fresh from one or more phases, for instance in multicomponent kit form, so as to avoid aging and to maximize the therapeutic effectiveness of the antimicrobial metal component. Formulations are best used within about 30 days after combining the phases. Suitable kits or containers are well known for maintaining the phases of formulations separate until the time of use. For instance, the antimicrobial metal in powder or coated substrate form may be packages separately from therapeutically acceptable carriers, and possibly other ingredients for mixing at the time of use. The separate coated substrate may be in dressing or patch form for direct application, or may take other suitable forms to generate liquid formulations and the like, such as a coating on the inside surface of a vial or container, a mesh, or a film. For example, the antimicrobial metal may be provided in a "tea bag"-type infuser or pouch, for generating liquid formulations at the time of use. The tea bag-type infuser is advantageous in that the pouch may serve as a filter for small particulates of the powder that may be detrimental to administration for some applications such as aerosols for respiratory disorders. A kit containing the dressing, coated substrate or powder may provide a sterile carrier such as water (and other ingredients) in a separate container in dosage specific amounts. As used herein, the term "kit" is meant to refer to packaged formulations, whether the ingredients are in separate phases or mixed, and thus for example, may include a gel in a tube with all ingredients in admixture, or any formulation wherein the ingredients are separated from each other.

For liquid formulations, in order to increase the amount of antimicrobial or noble metal solubilized in the solution, the pH of the solution during dissolution may be lowered to less than pH 6.5, more preferably to the range of 3.5 to 6.5, with such acidifying agents as carbon dioxide (which generated carbonic acid in solution). This pH range will typically generate concentrations of silver from atomic disordered silver from 85 µg/ml to 370 µg/ml, and can be adjusted for different desired concentrations. Dissolution of the antimicrobial metal will typically raise the pH to 6.5 to 7.0.

Administration as aerosols produces droplets preferably less than 10 µm in size, more preferably less than 5 µm in size, most preferably 1–3 µm in size. Control of the droplet size is important both to control the dosage delivered and to enhance delivery to the target tissue; thus, depending on the dosage required and the target tissue, it may be important to regulate the droplet size of the aerosol. In this respect, it has been found that droplet size can be regulated, to at least some extent, by the mechanical mister which is used to produce the aerosol. In addition, the aerosol's droplet size can be adjusted, to at least some extent, by modifying the surface tension of the solution. More particularly, the solution of the antimicrobial metal typically has water as its solvent, and water has a relatively high surface tension, so it is relatively straightforward to create an aerosol having relatively small droplet size. Surface active agents can be added to the solution so as to reduce the surface tension of the solution, whereby to create an aerosol having a relatively large droplet size. By way of example, such surfactants may comprise sodium alkyl sulfates, sodium laryl sulfate, sodium lauroyl sarconsinate, phospholipids, e.g., lecithin, sphingomyelin, etc.

Depending on the application, solutions generated from powders of the antimicrobial metal should avoid inclusion of particulates larger than 2 µm, and more preferably no larger than 1 µm (i.e., submicron) to avoid deleterious immune responses or toxic effects. Larger particulates may be removed by, for example filtration. Particulates may be formed in the liquid and can be removed, for example by filtration. For instance, silver carbonates may be formed on reaction with the carbonic acid used to acidify the solution. Particulate generation may also be limited by diluting the carbonic acid in solution.

The aerosol may be created by passing a liquid solution of the antimicrobial metal through a mechanical mister (e.g., a nebulizer) and may be applied directly with a pressurized pack (e.g., via a hand inhaler with a propellant such as carbon dioxide or other gas, with a valve metered dosage) or through some other delivery system (e.g., an oxygen tent, etc.).

The invention provides methods of treatment by administering a therapeutically effective amount of a nanocrystalline antimicrobial or noble metal powder, or a solution derived from a nanocrystalline antimicrobial or noble metal, as either a topical formulation, or as a coating on medical dressing, applied to the locally affected area of the skin. A therapeutically effective amount may be determined by testing formulations containing the nanocrystalline antimicrobial or noble metals by in vitro or in vivo testing. Formulations may be applied one or more times a day. Dressings coated with the nanocrystalline antimicrobial or noble metals may be changed daily, or even less frequently, and should be kept in a moist condition with the addition of saline, alcohols, or more preferably sterile water, in order to release ions, atoms, molecules or clusters of the nanocrystalline metal, on a sustained basis.

E. EXAMPLES

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value. The coating layers were formed by magnetron sputtering under the conditions set out in Table 1.

TABLE 1

Sputtering conditions

| Sputtering Conditions | Base Layer | Top Layer |
| --- | --- | --- |
| Target | 99.99% Ag | 99.99% Ag |
| Target Size | 20.3 cm diameter | 20.3 cm diameter |
| Working Gas | 96/4 wt % Ar/$O_2$ | 96/4 wt % Ar/$O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr ($4 \times 10^{-4}$ Pa) | $3.0 \times 10^{-6}$ Torr ($4 \times 10^{-4}$ Pa) |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of *Staphylococcus aureus* ATCC No. 25923. The inoculant was prepared from Bactrol Discs (Difco, M.), which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition−diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility≦1 mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, before packaging. Alternatively, the dressings may be packaged with instructions for the patient or clinician to cut the dressing to size.

Additional silver coated dressings were prepared in a full scale roll coater under conditions to provide coatings having the same properties set out above, as follows:

i the dressing material included a first layer of silver coated DELNET, as set out above, laminated to STRATEX, AET, 8.0NP$_2$-A/QW, which is a layer of 100% rayon on a polyurethane film.

ii Silver Foam Dressing—three layers of silver coated high density polyethylene prepared as above, alternating with two layers of polyurethane foam, L-00562-6 Medical Foam, available from Rynel Ltd., Bootbay, Me., USA.

The HDPE mesh coated with silver can be used to generate solutions containing silver species for liquid formulations and the like.

Example 2

Preparation of Nanocrystalline Silver Coating on HDPE Mesh

The silver coated mesh was produced, as set forth in Example 1, by sputtering silver onto Delnet, a HDPE mesh (Applied Extrusion Technologies, Inc., Middletown, Del., USA) using Westaim Biomedical TMRC unit under the following conditions:

TABLE 2

| Sputtering conditions | |
|---|---|
| Target | 99.99% Ag |
| Target Size | 15.24 cm × 152.4 cm |
| Working Gas | 99.375:0.625 wt % Ar/O$_2$ |
| Working Gas Pressure | 5.33 Pa (40 mT) |
| Total Current | 22 A |
| Base Pressure | 5.0 × 10$^{-5}$ Torr (6.6 × 10$^{-3}$) |
| Web Speed | 577 mm/min |
| Voltage | 367 V |

The coating was tested and found to have a weight ratio of reaction product to silver of between 0.05 and 0.1. The dressing was non-staining to human skin.

Example 3

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended metal scrapers as the belt rounded the end rollers. For the coated silicon wafers, the coatings were scraped off with a knife edge. The sputtering conditions were as follows:

TABLE 3

| Sputtering Conditions | |
|---|---|
| Target | 99.99% Ag |
| Target Size (individual, 23 targets) | 15.24 cm × 1216.125 cm |
| Working Gas | 75:25 wt % Ar/O$_2$ |
| Working Gas Pressure | 5.33 Pa (40 mT) |
| Total Current | 40 A |
| Base Pressure | 5.0 × 10$^{-5}$ Torr (range: 1 × 10$^{-4}$ – 9 × 10$^{-7}$ Torr or 1 × 10$^{-2}$ – 1.2 × 10$^{-4}$ Pa) |
| Sandvik Belt Speed | 340 mm/min |
| Voltage | 370 V |

Note - pressure conversions to Pa herein may not be accurate, most accurate numbers are in torr, mTorr units.

The powder had a particle size ranging from 2 μm to 100 μm, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

Example 4

In vitro Activity of Silver Solution Against *Propionibacterium Acne*

An in vitro test was conducted to determine if silver solutions according to the present invention effectively control *Propionibacterium acne*. The silver solution was obtained by static elution of Acticoat™ Burn Wound Dressing (lot#: 00403A-05, Westaim Biomedical Corp., Fort Saskatchewan, Canada) with nanopure water in a ratio of one square inch of dressing in five milliliters of water for 24 hours at room temperature. The silver concentration of the silver solution was determined by an atomic absorption method. The silver elute was diluted with nanopure water to 20 μg/ml. The *Propionibacterium acne* (ATCC No. 0919) was provided by Biofilm Research Group, University of Calgary.

The inoculum was prepared by inoculating freshly autoclaved and cooled tubes of Tryptic soy broth (TSB) with P. acne and incubating them for 2 days at 37° C. in an anaerobic jar. At this time, the optical density of the suspensions was ~0.3 at a wavelength of 625 nm.

The bacterial suspension (100 μL) was mixed with 100 μL of the silver solution being tested. The final concentration of silver in these mixtures was 10 μg/ml. The mixtures were incubated in an anaerobic jar at 37° C. for two hours. The silver was neutralized by addition of 0.4% STS (0.85% NaCl, 0.4% Sodium thioglycolate, 1% Tween™ 20) and the solution was serially 10-fold diluted with phosphate-buffered saline. 20 μL aliquots of the original solution and subsequent dilutions were plated onto TSA drop plates. The drops were allowed to dry and the plates were incubated in an anaerobic jar at 37° C. for 72 hours at which time the colonies were counted. The control consisted of 100 μL of bacterial suspension mixed with 100 μL of nanopure water and treated as above.

The results showed that the silver solution according to the present invention, at a final concentration of 10 μg/ml, gave 4.3 logarithm reduction in viable P. acne counts in two hours.

Example 5

Treatment of Acne

A sixteen year old female was diagnosed with acne vulgaris. She had numerous red papules and pustules on her forehead. Various skin cleansing regimes and antibiotic (erythromycin and clindomycin) treatments had been tried and had failed to control the acne. Prior to bed time, the papules and pustules on one side of her forehead were moistened and covered with a nanocrystalline silver coated high density polyethylene mesh, prepared as in Example 1 (single layer, blue coating). The mesh was then occluded with a thin film dressing which remained in place for 10 hours. Upon removal, the papules and pustules were no longer red and were only slightly raised. Some brown staining of the skin was observed.

Example 6

Treatment of Acne

A sixteen year old male was diagnosed with acne vulgaris. He had numerous raised, red papules and pustules on his forehead. Various skin cleansing regimes and antibiotic treatments had been tried and had failed to control the acne. The patient was placed on isotretinoin treatment which controlled his acne well. He did develop a single large pustule on his forehead which was embarrassing for him. Prior to bed time, the pustule was moistened and covered with a nanocrystalline silver coated high density polyethylene mesh prepared as in Example 2. The mesh was then occluded with a thin film dressing which remained in place for 10 hours. Upon removal the pustule was no longer red and was only slightly raised. A second treatment resulted in the disappearance of the pustule.

Example 7

Treatment of Acne

A sixteen year old female was diagnosed with acne vulgaris. She had numerous red papules and pustules on her forehead. Various skin cleansing regimes and antibiotic (erythromycin and clindomycin) treatments had been tried and had failed to control the acne. Prior to bed time, the papules and pustules on one side of her forehead were moistened and covered with a nanocrystalline silver coated high density polyethylene mesh, prepared as in Example 2. The mesh was then occluded with a thin film dressing which remained in place for 10 hours. Upon removal the papules and pustules were no longer red and were only slightly raised. A second treatment resulted in the disappearance of the papules and virtual elimination of the pustules. The silver coated mesh, when prepared as set forth in Example 2, did not result in any staining of the skin.

Example 8

Treatment of Adult Acne with Silver-Impregnated Hydrocolloid Dressing

A 49 year old white male experienced occasional acne vulgaris. He had painful, raised, red papules and pustules on his shoulders. The patient was treated with a thin hydrocolloid dressing (Craig Medical Products Ltd., Clay Gate House 46 Albert Rd. North Reigate, Surrey, United Kingdom) which was impregnated with 1% nanocrystalline silver powder formed with atomic disorder as in Example 3. Following cleansing, the pustule was covered with a small disc of the dressing, which remained in place for 24 hours. Upon removal, the pustule was no longer painful, red, or raised.

Example 9

Treatment of Eczema

A twenty-nine year old white female presented with acrodermatitis. The erythematous area was located on the dorsal surface of the first web space of the left hand. It was bounded by the metacarpal bones of the thumb and index finger. The patient also complained of pruritus associated with the dermatitis. A gel consisting of 0.1% nanocrystalline silver powder (formed with atomic disorder as in Example 3) and 2% carboxymethylcellulose was applied to the inflamed area before bedtime. There was an immediate antipruritic effect that provided the patient with relief in the short term. The next morning all evidence of acrodermatitis (i.e. redness disappeared) was gone. The condition had not returned after two weeks.

Example 10

Allergic Contact Dermatitis

Skin allergic contact hypersensitivity is caused by excessive infiltration of eosinophils. An animal model may be used for in vivo evaluation of eosinophil infiltration in the contact sensitivity reaction and to determine whether it is associated with allergic skin conditions such as contact dermatitis. On a gross histology level, this can be measured by the degree of erythema and edema at the dermatitis site. Current drugs used for treatment of this and other related eczema conditions include high potency steroids (Ultravate™), medium potency steroids (Elocon™) and non steroidal anti-inflammatory compounds (Protopic™ or tacrolimus). These compounds do not always work and may have undesirable side effects. Several commercially available anti-inflammatory products were compared to a nanocrystalline silver powder for the treatment of allergic contact dermatitis as follows.

Four healthy domestic pigs (approximate weight 20 kg) were used in the study. All pigs had normal skin prior to induction of eczema with 10% 2,4-dinitrochlorobenzene (DNCB) in acetone. The animals were housed in appropriate animal facilities with 12 hour light-dark cycles. The pigs were fed antibiotic-free feed and water ad libitum. The pigs were housed and cared for in accordance with Canadian Council of Animal Care guidelines. On day 0, the hair on both left and right back and side were clipped. The DNCB solution was painted over this area. This was repeated on day 7 and 11. On day 11, the solution was painted approximately 4 hours before treatment was initiated.

Treatment groups are shown in Table 4. Protopic™ (tacrolimus), Elocon™ and Ultravate™ were purchased as creams from the local pharmacy. The nanocrystalline silver powder (1 g/L) was mixed into a 2% sodium carboxymethyl cellulose (CMC) and water solution at 30° C. using a magnetic stirrer at a high speed (Vista Scientific). Petrolatum, commercially known as Vaseline™, was used as a control for Elocon™ and Ultravate.

TABLE 4

Treatment Groups

| Pig # | Treatment (Left side) | Control (Right side) | Day of Treatment |
|---|---|---|---|
| 1 | Protopic ™ (tacrolimus) | Protopic ™ Control | Day 0 |
| 2 | Medium Potency Steroid (Elocon ™) | Petrolatum | Day 0 |
| 3 | 2% CMC + 1% nanocrystalline silver (Vista Scientific) | 2% CMC | Day 11 |
| 4 | High Potency Steroid (Ultravate ™) | Petrolatum | Day 11 |

Pigs were placed under general anesthetic with ketamine (Ketalean™, MTC Pharmaceuticals, Cambridge, ON; 4–500 mg) and halothane (MTC Pharmaceuticals). The skin was wiped with a moist gauze and allowed to dry. Bandages (n=8) containing each treatment were applied to the left side of the thoracolumbar area of the pig, while control bandages (n=8) were applied to the right side of the thoracolumbar area of the pig. Following placement of bandages, they were covered with Tegaderm™ (3M Corp., Minneapolis, Min.) which was secured with an Elastoplast™ (Smith and Nephew, Lachine, QC) wrap. Bandages with active agents were changed daily. The skin associated with each bandage site was scored for severity of erythema (0=normal, 1=slight, 2=moderate, 3=severe, 4=very severe) and swelling (0=normal, 1=slight, 2=moderate, 3=severe, 4=very severe). This was performed on days 0, 1, 2 and 3.

Figure 2:
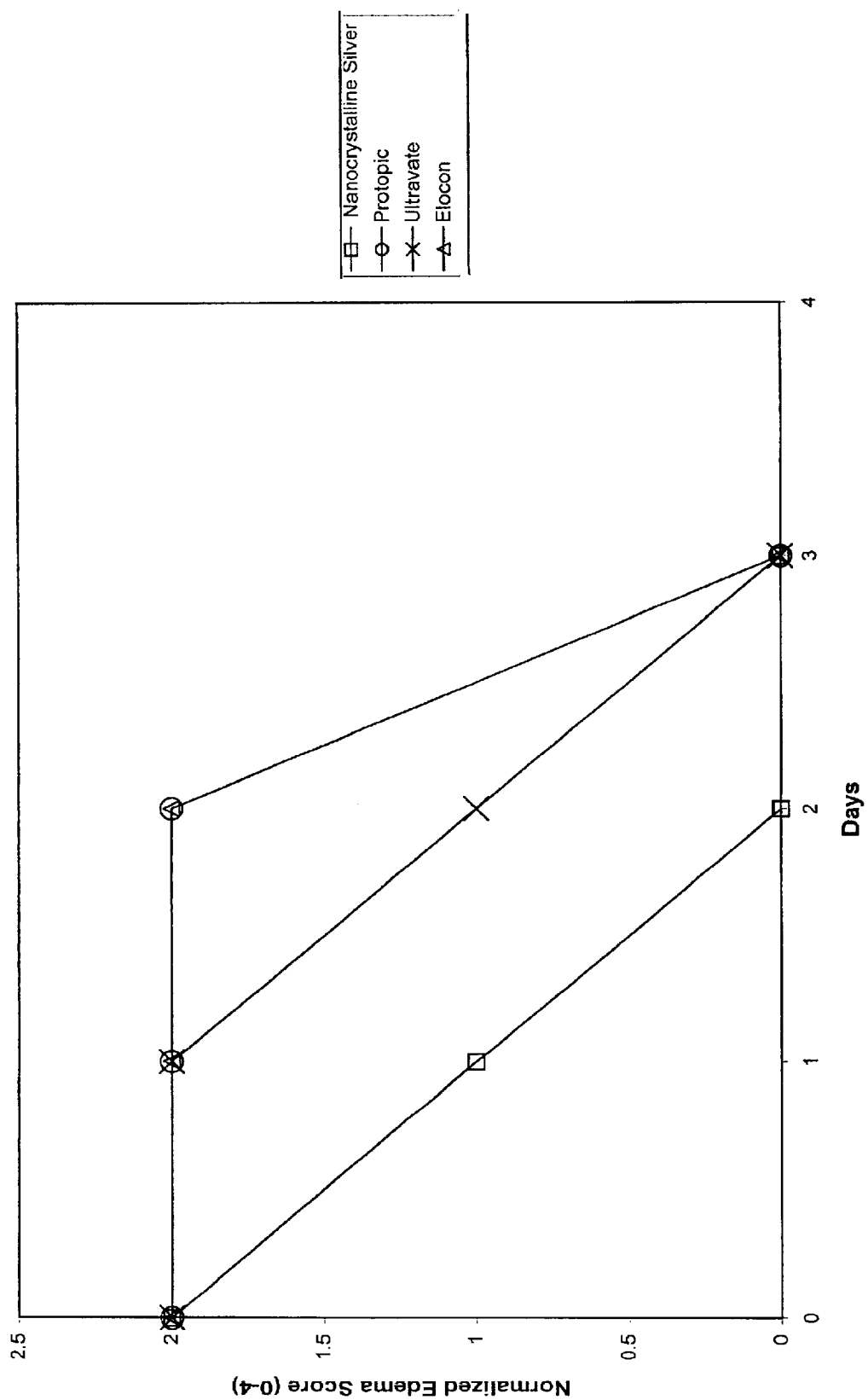
FIG. 2 is a graph showing the efficacy of the nanocrystalline silver powder compared to Protopic™ or tacrolimus (non-steroidal anti-inflammatory), Elocon™ (medium strength steroid) and Ultravate™ (high strength steroid), on edema.

All pigs remained healthy during the study. Results are shown in Tables 5 and 6, and indicated in FIGS. 1 and 2. FIGS. 1 and 2 show the efficacy of the nanocrystalline silver powder compared to Protopic™, Elocon™ and Ultravate™ in the treatment of contact dermatitis in the pig model.

TABLE 5

Results of Effects of Treatments Upon Erythema

| Treatment | Day 0 | Day 1 | Day 2 | Day 3 |
|---|---|---|---|---|
| Nanocrystalline silver | 3 | 2 | 1 | 0 |
| Protopic ™ | 3 | 3 | 1.9 | 0.4 |
| Elocon ™ | 3 | 2.4 | 2.6 | 2.6 |
| Ultravate ™ | 3 | 3 | 3 | 3 |

TABLE 6

Results of Effects of Treatments Upon Edema

| Treatment | Day 0 | Day 1 | Day 2 | Day 3 |
|---|---|---|---|---|
| Nanocrystalline silver | 2 | 1 | 0 | 0 |
| Protopic ™ | 2 | 2 | 2 | 0 |
| Elocon ™ | 2 | 2 | 2 | 0 |
| Ultravate ™ | 2 | 2 | 1 | 0 |

The pigs treated with the high (Ultravate™) and medium (Elocon™) strength steroids showed little to no improvement in the degree of erythema associated with contact dermatitis. They did, however, improve in terms of edema in that at Day 3, no swelling was apparent. Protopic™ showed a marked improvement when compared to the steroids in both the degree of erythema and edema. The largest improvement occurred with the nanocrystalline silver powder suspended in a 2% carboxymethyl cellulose gel. Both erythema and edema scores were lower after a single treatment and were normal after Day 2 (edema) and Day 3 (erythema) of treatment. Clearly the nanocrystalline silver product was more efficacious in treating contact dermatitis than the commercially available products.

Example 11

Preparation of Gels

No. 1

A commercial carboxymethyl cellulose/pectin gel (DuoDERM™, ConvaTec Canada, 555, Dr. Frederik Philips, Suite 110, St-Laurent, Quebec, H4M 2X4) was combined with nanocrystalline silver powder prepared as set forth in Example 3 to produce a gel with 0.1% silver. A logarithmic reduction test was performed as follows in the gel using *Pseudomonas aeruginosa*. The inoculum was prepared by placing 1 bacteriologic loopful of the organism in 5 mL of trypticase soy broth and incubating it for 3–4 h. The inoculum (0.1 mL) was then added to 0.1 mL of gel and vortexed (triplicate samples). The mixture was incubated for one-half hour. Then 1.8 mL of sodium thioglycollate-saline (STS) solution was added to the test tube and vortexed. Serial dilutions were prepared on 10o1 to 10–7. A 0.1 mL aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated. The logarithmic reduction for this mixture was 6.2, indicating a significant bactericidal effect.

No. 2

Carboxymethyl cellulose (CMC) fibers were coated directly to produce an atomic disordered nanocrystalline silver coating, using magnetron sputtering conditions similar to those set forth in Example 1. The CMC was then gelled in water by adding 2.9 g to 100 mL volume. This material was tested using the method of No. 1. The material generated a 5.2 logarithmic reduction of Pseudomonas aeruginosa, demonstrating that the gel had a significant bactericidal effect.

No. 3

An alginate fibrous substrate was directly coated with an atomic disordered nanocrystalline silver coating using magnetron sputtering conditions similar to those set forth in Example 1. The alginate (5.7 g) was added to 100 mL volume of water to create a gel. This material was tested using the method of No. 1. The material generated a 5.2 logarithmic reduction of *Pseudomonas aeruginosa*, demonstrating that the gel had a significant bactericidal effect.

No. 4

A commercial gel containing CMC and alginate (Purilin gel, Coloplast) was mixed with a atomic disordered nanocrystalline silver powder to give a product with 0.1% silver. This was tested as above with both *Pseudomonas aeruginosa* and *Staphylococcus aureus*. Zone of inhibition data was also generated for this gel as follows. An inoculum (*Pseudomonas aeruginosa* and *Staphylococcus aureus*) was prepared as in No. 1 and 0.1 mL of this was spread onto the surface of Mueller-Hinton agar in a Petri dish. A six mm hole was then cut into the agar at the center of the Petri dish and removed. The well was filled with either 0.1 mL of the silver containing gel, a mupirocin containing cream or a mupirocin containing ointment. The Petri plates were then incubated for 24 h and the diameter of the zone of inhibition was measured and recorded.

The silver containing gel produced 9 mm zone of inhibition against both *Pseudomonas aeruginosa* and *Staphylococcus aureus*, while the mupirocin cream and ointment produced 42 and 48 mm zones against *Staphylococcus aureus* and 0 mm zones against *Pseudomonas aeruginosa*.

The silver containing gel reduced the *Pseudomonas aeruginosa* and *Staphylococcus aureus* properties by 4.4 and 0.6 log reductions, respectively, showing good bactericidal activity. The mupirocin cream and ointment generated 0.4 and 0.8, and 0.8 and 1.6, log reductions against *Staphylococcus aureus* and *Pseudomonas aeruginosa*, respectively. The silver gel had both a greater bactericidal effect and spectrum of activity than the mupirocin containing products.

Nos. 5–10

The formula for Nos. 5–10 are summarized in Table 7. Zones of inhibitions were mined as in No. 4 and log reductions were determined as in No. 1.

All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa*, respectively.

TABLE 7

Formulae for Gel Nos. 5–10 and Efficacy Results

| # | CMC (%) | PVA (%) | Silver Powder (%) | β-glucan | Methyl paraben | Propyl paraben | CZOI S. aureus | CZOI P. aeruginosa | Log Red'n S. aureus | Log Red'n P. aeruginosa |
|---|---|---|---|---|---|---|---|---|---|---|
| 5 | 2 | | 0.1 | | | | 11 | 13 | 1.4 | >6 |
| 6 | 2 | 0.5 | 0.1 | | 0.1 | 0.02 | 14 | 15 | 3.3 | >6 |
| 7 | 2 | 0.5 | 0.1 | | | | 13 | 14 | 2 | N/A |
| 8 | 2 | 0.5 | 0.1 | | 0.1 | | 14 | 14 | 2 | N/A |
| 9 | 2 | 0.5 | 0.1 | | | 0.20 | 14 | 14 | 2 | N/A |
| 10 | 2 | 0.5 | 0.1 | 0.5 | 0.1 | 0.20 | 14 | 14 | 2 | >6 |

No. 11

A commercially available gel (glyceryl polymethacrylate) was blended with nanocrystalline silver powder to produce a gel with a silver content of 0.1%. This gel was tested as in Nos. 5–10 and was found to produce zones of 15 mm against both *Staphylococcus aureus* and *Pseudomonas aeruginosa*. Log reductions of 1.7 and >5 were produced against *Staphylococcus aureus* and *Pseudomonas aeruginosa*. This gel product had a greater spectrum of activity than did mupirocin cream or ointment.

Example 12

Treatment of Adult Acne with Nanocrystalline Silver Gel Occluded by a Hydrocolloid Dressing A 49 year old white male experienced occasional acne vulgaris. He had painful, raised, red papules and pustules on his shoulders. The patient was treated with gel formulation No. 5 as set forth in Example 11. Gel formulation No. 5 was applied to the problem area of the patient's shoulders and then occluded by a thin hydrocolloid dressing (Craig Medical Products Ltd., Clay Gate House 46 Albert Rd. North Reigate, Surrey, United Kingdom). The dressing remained in place for 24 hours. Upon removal the pustule was no longer painful, red, or raised.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A method of reducing inflammation of an inflammatory skin condition which comprises:

contacting an inflammatory problem area of a patient with said condition, with a therapeutically effective amount of one or more antimicrobial metals in crystalline form to provide a localized anti-inflammatory effect, wherein the one or more antimicrobial metals are characterized by sufficient atomic disorder so that the one or more antimicrobial metals, when in contact with an alcohol or water-based electrolyte, releases atoms, ions, molecules, or clusters of the one or more antimicrobial metals on a sustainable basis, wherein said condition is selected from the group consisting of a form of eczema, contact irritant dermatitis, seborrheic dermatitis, an insect bite, an insect sting, sunburn, mycosis fungoides, pyoderma gangrenosum and rosacea.

2. The method as set forth in claim 1, wherein the one or more antimicrobial metals further provide a localized antimicrobial effect.

3. The method as set forth in claim 1, wherein the antimicrobial metal is selected from the group consisting of silver, gold, platinum and palladium.

4. The method as set forth in claim 3, wherein the condition is a form of eczema.

5. The method as set forth in claim 3, wherein the antimicrobial metal is nanocrystalline silver.

6. The method as set forth in claim 4, wherein the antimicrobial metal is silver, formed as a composite with oxygen.

7. The method as set forth in claim 3, wherein the condition is a form of eczema selected from the group consisting of atopic eczema, acrodermatitis eczema, contact allergic dermatitis, dyshydrotic eczema, lichen simplex chronicus, nummular eczema, and statis eczema.

8. The method as set forth in claim 3, wherein the one or more antimicrobial metals are provided as a coating on, or filler in, a dressing, or in a pharmaceutical composition with one or more pharmaceutically and dermatogically acceptable carriers, diluents, or excipients suitable for topical application.

9. The method as set forth in claim 8, wherein the pharmaceutical composition includes a nanocrystalline powder of the one or more antimicrobial metals, or a solution containing dissolved species from a nanocrystalline powder or coating of one or more antimicrobial metals.

10. The method as set forth in claim 9, wherein the pharmaceutical composition is a gel, cream, lotion, paste or ointment containing the antimicrobial metal powder in an amount of 0.01–10% by weight, or a liquid formulated as a topical solution, spray, mist, or drops containing 0.001–10% by weight of the antimicrobial metal.

11. The method as set forth in claim 10, wherein the antimicrobial metal is nanocrystalline silver.

12. The method as set forth in claim 10, wherein the antimicrobial metal is silver, formed as a composite with oxygen.

13. The method of claim 8, wherein the dressing or pharmaceutical composition is fixed in place or occluded with an occlusive or semi-occlusive layer which maintains the dressing or composition in a moist condition.

14. The method as set forth claim 8, wherein the coating is provided on a dressing.

15. The method as set forth in claim 8, wherein the coating is 150–3000 nm thick.

16. The method as set forth in claim 9, wherein the one or more antimicrobial metals are provided in a hydrated dressing.

17. The method as set forth in claim 10, wherein the gel, cream, lotion, paste, or ointment is occluded by a hydrated dressing.

18. The method as set forth in claim 16 or 17, wherein the hydrated dressing is selected from the group consisting of a hydrocolloid, hydrogel, polyethylene, polyurethane, polyvinylidine, siloxane and silicone dressing.

19. The method as set forth in claim 18, wherein the hydrated dressing is a hydrocolloid dressing.

20. The method as set froth in claim 19, wherein the hydrocolloid dressing contains a hydrocolloid selected from the group consisting of alginates, starch, glycogen, gelatin, pectin, chitosan, chitin, cellulose and derivatives thereof, gum Arabic, locust bean gum, karaya gum, gum tragacanth, ghatti gum, agar-agar, carrageenans, carob gum, guar gum, xanthan gum, and glyceryl polymethacrylate.

21. The method as set forth in claim 20, wherein the hydrocolloid is one or more of carboxymethyl cellulose, alginates, pectin and glyceryl polymethacrylate.

22. The method of claim 4, wherein the antimicrobial metal is in a powder form and is delivered directly to the skin.

23. The method of claim 22, wherein the powder is sized with particulates no larger than 2 μm.

24. The method of claim 23, wherein the powder is sized with particulates no larger than 1 μm.

25. The method of claim 24, wherein the antimicrobial metal is nanocrystalline silver.

26. The method of claim 24, wherein the antimicrobial metal is nanocrystalline silver, formed as a composite with oxygen.

27. The method as set forth in claim 1, wherein the condition is a form of eczema.

28. The method as set forth in claim 27, wherein the condition is a form of eczema selected from the group consisting of atopic eczema, acrodermatitis eczema, contact allergic dermatitis, dyshydrotic eczema, lichen simplex chronicus, nummular eczema, and statis eczema.

29. The method as set forth in claim 1, wherein the antimicrobial metal is nanocrystalline silver, formed as a composite with oxygen.

30. The method as set forth in claim 1, wherein the pharmaceutical composition includes a nanocrystalline powder of the one or more antimicrobial metals, or a solution containing dissolved species from a nanocrystalline powder or coating of one or more antimicrobial metals.

31. The method as set forth in claim 1, wherein the pharmaceutical composition is a gel, cream, lotion, paste or ointment containing the antimicrobial metal powder in an amount of 0.01–10% by weight, or a liquid formulated as a topical solution, spray, mist, or drops containing 0.001–10% by weight of the antimicrobial metal.

32. The method as set forth in claim 1, wherein the antimicrobial metal is silver, formed as a composite with oxygen.

33. The method as set forth in claim 1, wherein the one or more antimicrobial metals are provided as a coating on, or filler in, a dressing, or in a pharmaceutical composition with one or more pharmaceutically and dermatogically acceptable carriers, diluents, or excipients suitable for topical application.

34. The method of claim 33, wherein the dressing or pharmaceutical composition is fixed in place or occluded with an occlusive or semi-occlusive layer which maintains the dressing or composition in a moist condition.

35. The method of claim 33, wherein the coating is provided on a dressing.

36. The method o claim 34, wherein the coating is 150–3000 nm thick.

37. The method of claim 33, wherein the one or more antimicrobial metals are provided in a hydrated dressing.

38. The method of claim 31, wherein the gel, cream, lotion, paste, or ointment is occluded by a hydrated dressing.

39. The method as set forth in claim 37 or 38, wherein the hydrated dressing is selected from the group consisting of a hydrocolloid, hydrogel, polyethylene, polyurethane, polyvinylidine, siloxane and silicone dressing.

40. The method as set forth in claim 39, wherein the hydrated dressing is a hydrocolloid dressing.

41. The method as set froth in claim 40, wherein the hydrocolloid dressing contains a hydrocolloid selected from the group consisting of alginates, starch, glycogen, gelatin, pectin, chitosan, chitin, cellulose and derivatives thereof, gum Arabic, locust bean gum, karaya gum, gum tragacanth, ghatti gum, agar-agar, carrageenans, carob gum, guar gum, xanthan gum, and glyceryl polymethacrylate.

42. The method as set forth in claim 41, wherein the hydrocolloid is one or more of carboxymethyl cellulose, alginates, pectin, and glyceryl polymethacrylate.

43. The method of claim 1, wherein the antimicrobial metal is in a powder form and is delivered directly to the skin.

44. The method of claim 42, wherein the powder is sized with particulates no larger than 2 μm.

45. The method of claim 42, wherein the powder is sized with particulates no larger than 1 μm.

46. The method of claim 42, wherein the antimicrobial metal is nanocrystalline silver.

47. The method of claim 42, wherein the antimicrobial metal is nanocrystalline silver, formed as a composite with oxygen.

48. The method of claim 1, wherein the condition is an insect bite.

49. The method of claim 1, wherein the condition is an insect sting.

50. The method of claim 1, wherein the condition is sunburn.

51. The method of claim 1, wherein the condition is mycosis fungoides.

52. The method of claim 1, wherein the condition is pyoderma gangrenosum.

53. The method of claim 1, wherein the condition is rosacea.

* * * * *